United States Patent [19]

Dougherty et al.

[11] Patent Number: 5,015,463

[45] Date of Patent: May 14, 1991

[54] METHOD TO DIAGNOSE THE PRESENCE OR ABSENCE OF TUMOR TISSUE

[75] Inventors: Thomas J. Dougherty; William R. Potter, both of Grand Island; Kenneth R. Weishaupt, Sloan, all of N.Y.

[73] Assignee: Health Research, Inc., Buffalo, N.Y.

[21] Appl. No.: 515,179

[22] Filed: Apr. 26, 1990

Related U.S. Application Data

[60] Continuation of Ser. No. 352,774, May 16, 1989, which is a continuation of Ser. No. 889,917, Jul. 24, 1986, Pat. No. 4,889,129, and a continuation of Ser. No. 889,829, Jul. 24, 1986, Pat. No. 4,866,168, which is a division of Ser. No. 609,991, May 14, 1984, Pat. No. 4,649,151, which is a continuation-in-part of Ser. No. 481,345, Apr. 1, 1983, abandoned, which is a continuation-in-part of Ser. No. 424,647, Sep. 27, 1982, abandoned, said Ser. No. 889,917, is a division of Ser. No. 609,991.

[51] Int. Cl.$^5$ ............................................. A61K 49/00
[52] U.S. Cl. ......................................... 424/7.1; 424/2; 424/9; 514/410; 540/145
[58] Field of Search ................ 424/2, 7.1, 9; 514/410; 540/145

[56] References Cited

U.S. PATENT DOCUMENTS 4,649,151 3/1987 Dougherty et al. ................ 514/410

Primary Examiner—Richard L. Raymond
Attorney, Agent, or Firm—Irell & Manella

[57] ABSTRACT

A photosensitizing composition prepared by recovering a portion of hematoporphyrin derivative which has aggregate weight of more than 10 kd is useful in locating tumor tissue to which this improved photosensitizing drug homes. In the invention method, the subject is administered the improved drug and sufficient time is allowed to pass to permit accumulation of the drug in tumor tissue. The subject is then illuminated at suspected sites with radiation capable of absorption by the improved drug and which radiation produces fluorescence by the drug. Detection of the intensity of fluorescence indicates the quantity of drug at the measured location and permits assessment as to whether a tumor is present at that location.

2 Claims, 15 Drawing Sheets

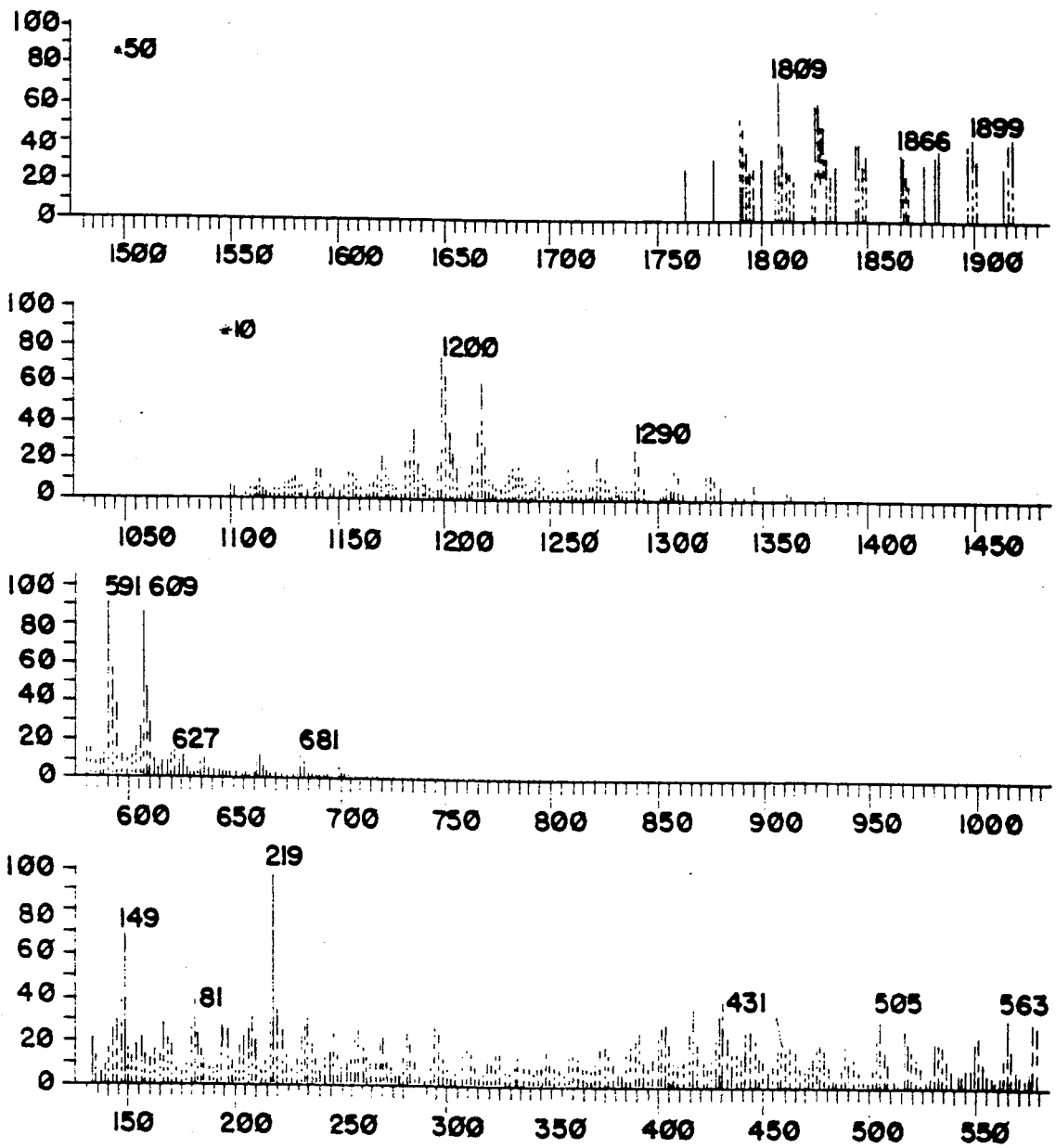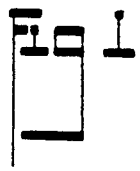

METHOD TO DIAGNOSE THE PRESENCE OR ABSENCE OF TUMOR TISSUE

RIGHTS IN THE UNITED STATES GOVERNMENT

This invention was made with federal support under research grants CA 30940-01 and CA 16717 and contract NO1-CM-97311, awarded by the National Cancer Institute, U.S. Department of Health and Human Services. The Government has certain rights to this invention.

RELATED CASES

This is a continuation of U.S. Ser. No. 352,774, filed May 16, 1989, which is a continuation of U.S. Ser. No. 889,917 filed July 24, 1986 and now U.S. Pat. No. 4,889,129, as well as a continuation of U.S. Ser. No. 889,829 filed July 24, 1986 and now U.S. Pat. No. 4,866,168; both said issued U.S. patents being divisional applications of U.S. Ser. No. 609,991 filed May 14, 1984 and now U.S. Pat. No. 4,649,151, which is a continuation-in-part of Ser. No. 481,345 filed Apr. 1, 1983 and abandoned, which is a continuation-in-part of Ser. No. 424,647 filed Sept. 27, 1982 and abandoned.

BACKGROUND OF THE INVENTION

This invention relates to the diagnosis and treatment of undesirable tissue such as malignant tumors by certain drugs that accumulate in the undesirable tissue.

In one class of diagnosis and treatment with photosensitizing drugs, tumors are detected and treated by irradiating the tumors with light after the drug accumulates in the tumor. The drugs are photosensitizing and some of the drugs in this class are derivatives of hemoglobin.

There are several prior art techniques for such diagnosis and treatment. For example, in "Etudes Sur Les Aspects Offerts Par Des Tumeur Experimentales Examinee A La Lumiere De Woods", CR Soc. Biol. 91:1423-1424, 1924, Policard, the author, noted that some human and animal tumors fluoresced when irradiated with a Wood's lamp. The red fluorescence was attributed to porphyrins produced in the tumor. In "Untersuchungen Über Die Rolle Der Porphine Bei Geschwulstkranken Menschen Und Tieren", Z Krebsforsch 53:65-68, 1942, Auler and Banzer showed that hematoporphyrin, a derivative of hemoglobin, would fluoresce in tumors but not in normal tissues following systemic injection into rats.

In "Cancer Detection Therapy Affinity of Neoplastic Embryonic and Traumatized Regenerating Tissue For Porphyrins and Metalloporphyrins", Proc Soc Exptl Biol Med. 68: 640-641, 1948, Figge and co-workers demonstrated that injected hematoporphyrin would localize and fluoresce in several types of tumors induced in mice. In "The Use of a Derivative of Hematoporphyrin in Tumor Detection", J Natl Cancer Inst. 26:1-8, 1961, Lipson and co-workers disclosed a crude material, prepared by acetic acid-sulfuric acid treatment of hematoporphyrin, said material having a superior ability to localize in tumors.

The photosensitive characteristic of tumor-selective porphyrin compounds also make them useful in the treatment of tumors. In "Photodynamic Therapy of Malignant Tumors", Lancet 2:1175-1177, 1973, Diamond and co-workers achieved tumor necrosis after lesion-bearing rats were injected with hematoporphyrin and exposed to white light. In "Photoradiation Therapy for the Treatment of Malignant Tumors", Cancer Res. 38:2628-2635, 1978, and "Photoradiation in the Treatment of Recurrent Breast Carcinoma", J Natl Cancer Inst. 62:231-237, 1979, Dougherty and co-workers reported using the crude Lipson hematoporphyrin derivative to accomplish photoradiation therapy on human patients.

The crude Lipson hematoporphyrin derivative has the ability to enter a variety of tissues and to be retained in tumor cells after it has mostly cleared the serum. Subsequent irradiation with red light excites the crude Lipson derivative which in turn excites oxygen molecules. The excited oxygen molecules exist for a microsecond—long enough to attack tumor cell walls and effect necrosis. In "Effects of Photo-Activated Porphyrins in Cell Surface Properties", Biochem Soc Trans 5:139-140, 1977, Kessel explained that cross-linking of proteins in tumor cell membranes causes leakage and eventual cell disruption.

The crude Lipson hematoporphyrin derivative has several disadvantages such as: (1) it enters normal tissue and causes unacceptable damage to the normal tissue when therapeutic light sufficient to treat large tumors is applied; (2) it does not clear normal tissue sufficiently soon and thus some patients are harmed by exposure to ordinary sunlight as much as thirty days following treatment with the drug; and (3) it does not have an optimum absorbance spectrum in a range that penetrates tissue most effectively.

SUMMARY OF THE INVENTION

Accordingly, an object of the invention is to provide a purified or novel photosensitizing drug that can be used to effect photoradiation location of neoplastic tissue and therapy of undesirable neoplastic tissue such as tumors or hyperproliferatic tissue.

A still further object of the invention is to provide purified or novel photosensitive drugs that are highly neoplastic-tissue selective.

A still further object of the invention is to provide novel photosensitive drugs that rapidly clear normal tissue but do not rapidly clear neoplastic tissue.

A still further object of the invention is to provide a neoplastic-tissue-selective drug that fluoresces, delineating malignancy and aiding in diagnosis.

A still further object of the invention is to provide a drug which is selective of certain pathogens within an animal or within blood, blood plasma or serum or fractions thereof and permit photochemical destruction of the pathogens in vivo or in vitro.

A still further object of the invention is to provide a novel method of producing the above-identified drugs.

A still further object of the invention is to provide novel method and equipment for the localization and/or treatment of tumors and certain other tissue.

A still further object of the invention is to provide a method and drugs for selectively entering cells for photodynamic or chemical action in conjunction with other agents.

In accordance with the above noted and other objects of the invention, photosensitizing, undesirable-tissue-selective drugs are obtained from phlorin or chlorin or other pyrrole-containing molecules. Generally, these drugs are neoplastic-tissue selective including hyperproliferatic tissue selective and tumors. These drugs are an effective in vivo photosensitizer and have the following properties: (1) they are retained in malignant tissue; (2) their molecules are not easily disaggregated from each other by serum protein; (3) they are efficient in producing a photochemical effect in vivo which is toxic to cells or tissue; (4) they absorb light at wavelengths which penetrate tissue; (5) they are relatively non-toxic in the absence of the photochemical effect in effective doses; (6) they are readily cleared from normal tissues; (7) they have a triplet energy state above 37.5 kilocalories; (8) they are not readily oxidized; (9) they don't readily quench required excited states; and (10) they are water soluble.

This drug is an improvement over earlier drugs because of its selectivity. This selectivity occurs in one embodiment because the drug has the ability to remain self-associated in serum at least to some degree for a certain period of time which is at least fifteen minutes and to bind within the cell. It is believed that the self-association causes the drug to be removed from normal tissue but retained in neoplastic tissue at least partly in some cases by the endothelial cells of the tumors as well as by the tumor cells in higher concentrations than in most normal tissue and for longer periods of time than in most normal tissue.

In addition to selectivity, the drug must dissociate in the tissue or in lipids before it is energized by radiation to damage the neoplastic tissue. This combination of self-association in serum and dissociation in lipids occurs, in one embodiment, because the individual molecules have sufficiently higher attraction for each other than for water to form aggregates of molecular weight greater than 10,000 and sufficient attraction for lipids compared to each other to dissociate in tissue.

The individual molecules each include two groups bound to each other each including four rings, some of which are pyrroles such as phlorins, porphyrins, chlorins or substituted phlorins, pyrroles or chlorins, each group forming a ring so that they have sufficient self-affinity to form aggregates of molecular weight above 10,000 in water, in isotonic saline and in the vascular system but may break down in neoplastic tissue and attach to the cell.

Moreover, other photosensitizing materials may be combined with a carrier that enters undesirable tissues and cells of the reticular endothelial system such as macrophages. These photosensitizing materials: (1) must have a triplet energy state above 37.5 kilocalories per mole; (2) cannot be easily oxidized; and (3) not physically quench any required energy state. Preferably, this photosensitizing material should be lipophlic.

In one embodiment, a known reagent is formed by hydrolysis of the reaction mixture of hematoporphyrin and acetic-sulfuric acids. A suitable drug is purified from this reagent by elimination of low molecular weight compounds by filtration through a microporous membrane. This drug contains porphyrins at least 50 percent of which, and preferably more than 90 percent of which have the emiprical formula of approximately $C_{68}H_{70}N_8O_{11}$ or $C_{68}H_{66}N_8O_{11}Na_4$.

Other derivatives may be formed from this compound and it is believed other compounds may be formed either from other natural porphyrins or by synthesis from other materials such as by polymerization of monomeric pyrroles by dipyrollic inter mediates, from pyrromethenes, from pyromethanes, from pyroketones, from open chain tetrapyrrolic intermediates, from bilanes, from oxobilanes and from bilines. They may also be derived from natural pigments such as chlorophyll and hemogloblin. Such suitable compounds are described more fully in *Porphyrins and Metalloporphyrins* by J. E. Falk and Kevin M. Smith, 1975, Elsevier Scientific Publishing Company, Amsterdam, N.Y. and Oxford, the disclosure of which is incorporated herein.

Generally, the drugs are composed of groups of pyrroles or substituted pyrroles combined in a pattern. That pattern includes as a basic grouping a structure which is phlorin or a group of four pyrroles or combinations of pyrroles and substituted pyrroles formed into a larger ring. Two such rings are covalently bound to form a pair of units each having four pyrrole groups or four groups at least some of which are pyrroles or substituted pyrroles. The molecules preferably have an absorption spectrum which is within the range of wavelengths between 350 nm and 1200 nm. The absorption spectrum should be tailored to the desired penetration such as, for example, being strong in the red or near infrared wavelengths (600–1200 nm) for large bulking tumors and in the green or blue wavelengths such as 488 or 514 nm for superficial undesirable tissue.

In use for therapy, the drug is caused to enter the subject, where it is cleared from normal tissue sooner than from abnormal neoplastic tissue. After the drug has cleared normal tissue but before it has cleared abnormal neoplastic tissue, the abnormal neoplastic tissue may be located by the luminescence of the drug in the abnormal neoplastic tissue. The fluorescence may be observed with low intensity light some of which is within the drugs' absorbance spectrum or higher intensity light, a portion of which is not in the drugs' absorbance spectrum. Similarly, the drug is absorbed and retained by certain pathogens after it has cleared normal tissue.

To destroy the abnormal neoplastic tissue or pathogens, a higher intensity light having a frequency within the absorbance spectrum of the drug is applied. A synergistic effect without substantial destruction of tissue by heat is achieved by applying heat before, during or after the light radiation is applied and thus the tissue should be heated above 39.5 degrees Celsius and preferably within the range of 40.5 and 45 degrees Celsius. The increase in temperature may be achieved by transmitting light near or in the infrared spectrum or microwaves to the tissue. The temperature change should be within two hours before or two hours after treatment with light.

In the alternative, higher power laser light within the absorption spectrum of the drug causes thermal destruction of tissue which is interactive with the photodynamic effect of the drug. This removes bulky tumors or obstructions by vaporization or vascular occlusion such as by coagulation of blood.

DESCRIPTION OF THE DRAWINGS

The above noted and other features of the invention will be better understood from the following detailed description, when considered with reference to the accompanying drawings, in which:

FIG. 1 is a mass spectrometry printout of a drug in its methyl ester form;

DETAILED DESCRIPTION

General Description of the Drug

Figure 2:
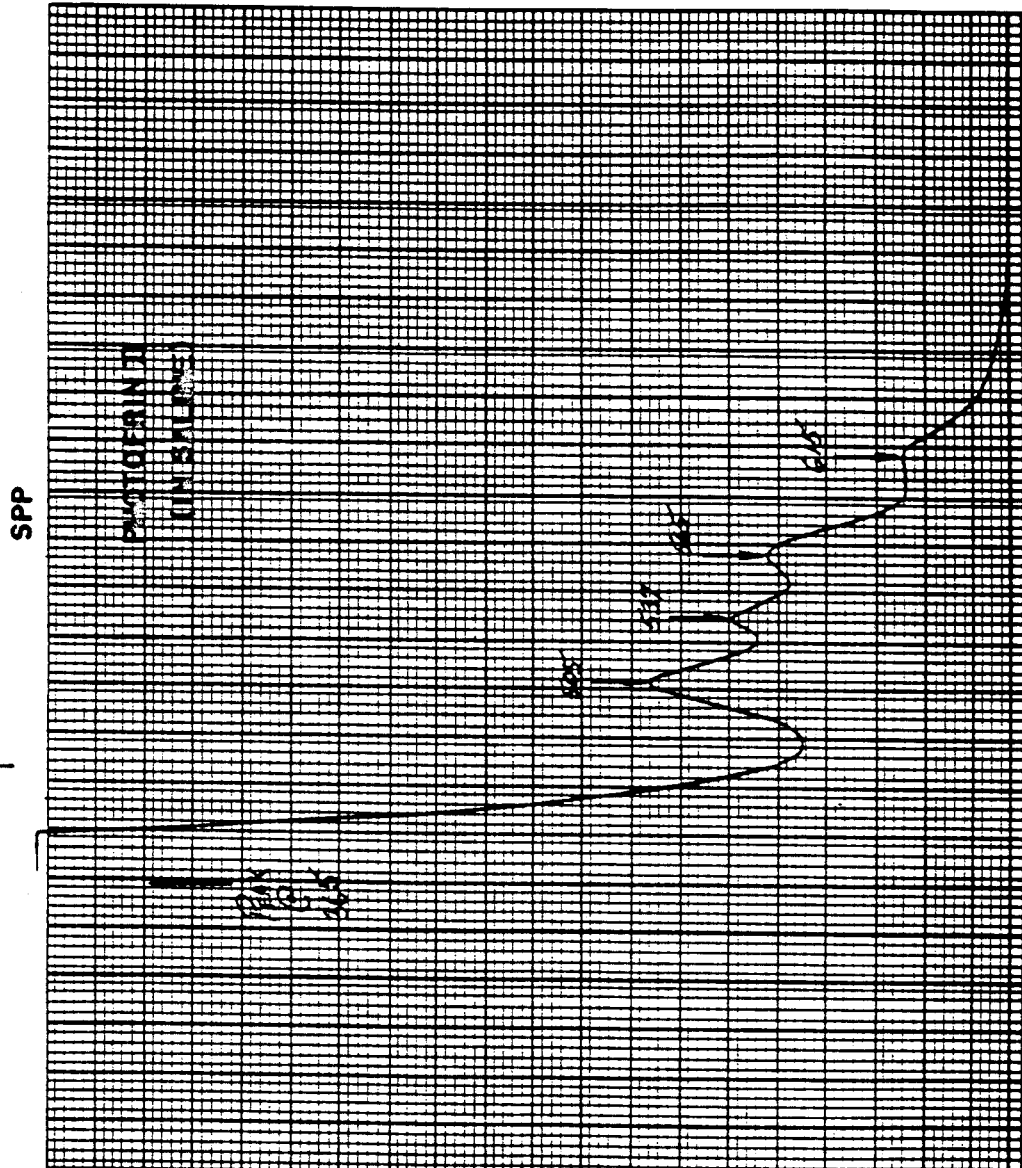
FIG. 2 is a visible light spectrum of a drug in a water solution.

Each of the drugs may be classified into one of two classes, which are: (1) each molecule of the drug aggregates in water to aggregates having a combined molecular weight of above 10,000; or (2) units of the drug are encapsulated in a liposome and molecules include at least one such photosensitizing chemical group.

The aggregates in the former class are sufficiently large and have characteristics which cause them to be removed by the lymphatic system so as to be excluded from most normal tissue and usually to enter and be retained by undesirable tissue, such as tumors. Because of the absence of a lymphatic system, the drug is not removed effectively from the tumors. The drugs of this invention bind within the cells to plasma membrane, nuclear membrane, mitochondria, and lysosomes. While it may enter some normal tissue, generally there is a sufficient difference in the rates of accumulation and removal between normal and undesirable tissue to provide selected conditions which permit treatment of undesirable tissue without excessive damage to normal tissue.

The form of drugs which aggregate must be sufficiently lipophlic to dissociate in lipids so that the aggregate is broken up within the tumor into a form which: (1) readily absorbs light within the light spectrum of 350 to 1,200 nm in wavelength; and (2) causes photodynamic effects. Thus, the drug is soluble in water to form large aggregates in aqueous suspension but sufficiently lipophilic to dissociate in neoplastic tissue.

At least one porphyrin utilized in the past by therapists as part of Lipson's reagent without knowing that it existed therein, has the necessary characteristics but in the prior art was utilized in a mixture of porphyrins which had deleterious side effects. It was not known that the substance was an effective agent in Lipson's reagent or that it existed therein because of its resistance to separation by liquid chromatography.

Reduced side effects are obtained from such a mixture of porphyrins when the mixture includes more than 50% of the drug and preferably 90% or more by weight of the porphyrins should be the drug or a drug having similar characteristics. With such a purified dosage, the porphyrins clear normal tissue adequately before the neoplastic tissue in which the drug has accumulated is exposed to light.

This drug (DHE) appears to be ineffective if it is in aggregates of molecular weight less than 10,000. Such lower molecular weight aggregates appear to be stable. Molecular weight of the aggregate in this application means the sum of the molecular weights of the molecules in an aggregate of molecules. An aggregate of molecules consists of a group of molecules bound together by forces other than covalent bonds.

Other drugs such as certain phlorins or chlorins have been used either with two groups bound together or single groups encapsulated in a liposome. In any drug, the drug must bind within the neoplastic tissue or release a drug that binds within the neoplastic tissue. More specifically, the drug includes compounds in which the individual molecules include two groups, each of which includes either phlorin or rings of pyrroles or hydrogenated pyrroles, or substituted pyrroles connected in such a way as to expose planes of both rings to other drug molecules.

With this structure, the attraction between molecules is greater than the attraction to water and thus molecules of the drug aggregate in aqueous suspensions. One such compound, dihematoporphyrin ether (DHE), purified from Lipson's reagent, is shown in formula 1 and another such compound, which is a chlorin, is shown in formula 2. The chlorin shown in formula 2 may be synthesized from chlorophyll or formed as a derivative from the compound of formula 1. The attraction to lipids is, however, sufficiently great to cause the aggregates to dissociate in a lipid environment. Metallo derivatives of the active compounds may be used, provided they do not interfere with the photosensitizing property of the molecules. For example, magnesium derivatives continue to work but copper derivatives do not.

General Description of Drug Preparation

First, for one embodiment, hematoporphyrin derivative is formed, using prior art methods or novel methods similar to prior art methods. This mixture contains a suitable drug. This suitable drug, when formed in the hematoporphyrin derivative, is normally in a mixture of other undesirable porphyrins.

To separate the effective drug from the undesirable porphyrins, the pH is raised into a range between 6.5 and 12 and preferably 9.5 to form an aggregate and then the material is separated. The separation may be by filtering, by precipitation, by gel electrophoresis, by centrifugation or by any other suitable means. For best results in filtering or other methods such as centrifugation based on the aggregate size, the pH is raised to 9.5 and filtering done at the high pH to remove other porphyrins rapidly and completely. The filter should retain aggregates of molecular weight above 10,000.

The pH must be adjusted during filtering because it tends to be reduced as the impurities are reduced. This is done by monitoring pH and adding an appropriate adjustor such as a base. To save time and water during purification, the concentration is increased to the lowest possible volume. This may, in an ideal system, be limited by solubility to prevent precipitation of the drug or the aggregation of undesirable substances.

In methods of separation based on affinity, a hydrophobic packing is used having a higher affinity for DHE than other porphyrins in hematoporphyrin derivative. DHE is selectively removed after other porphyrins with a solvent higher than alcohol in the eluantrophic series for reverse phase chromatography. More specifically, an inverse phase chromatographic column with packing of 5 micron spheres is used. THF may be used as the solvent.

Of course, the drug formed from hematoporphyrin derivative may be formed by other methods. In the preferred embodiment the drug is DHE, which is separated from hematoporphyrin derivative. However, DHE may be formed other ways and other compounds may be formed by other methods including from combinations of pyrroles or substituted pyrroles. For example, a drug similar to DHE may be formed using other formation bonds than the oxygen bond or from other hematoporphyrin derivatives and thus not be ethers. Moreover, such compounds may be synthesized instead from other feedstocks and still other compounds having the desired characteristics may be formed from other compounds such as chlorophylls.

A chlorin, the structure of which is not entirely known, has been combined with DHE and shown to have some effect in vivo when light in its absorbance spectrum was used. Better results have been obtained by encapsulating the same chlorin in liposome prepared using the method described by Dr. Eric Mayhew, "Handbook of Liposome Technology", Vol II, CRC Press, ed. G. Gregoriodis, the disclosure of which is incorporated herein. A molar ratio of 1:4:5 of egg phosphatidyl, glycerol, phosphatidyl choline, cholesterol was used.

General Description of Treatment

For treatment, a photosensitizing drug is injected into the subject which drug includes a plurality of molecules that: (1) aggregate in an aqueous suspension into groups having a molecular weight above 10,000 or are encapsulated in another material that enters cells; and (2) dissociate and attach themselves in neoplastic tissue. The drug is then permitted to clear normal tissue and the neoplastic tissue is exposed to electromagnetic radiation having a power at a value in a range of between 5 milliwatts per square centimeter and 0.75 watts per square centimeter without thermal effects in a wavelength band of between 350 nm and 1,200 nm to destroy the vascular system and other tissue within the neoplastic tissue that has accumulated the drug.

In treating humans or other mammals with the drug, light is irradiated on the tissue in such a position as to uniformly illuminate the cancer tissue. A synergistic effect is obtained by applying heat either before, during or after the light to heat the tissue above 39.5 degrees Celsius and preferably within the range of 40.5 to 45 degrees Celsius.

The increase in temperature, when used, may be achieved by transmitting light: (1) some of which is near or in the infrared spectrum such as at 1060 nm wavelength from a Nd-Yag laser for heat with the light at 630 nm for interaction with the photosensitive drug; or (2) by microwaves such as at 2450 MHz; or (3) by any other suitable means. The temperature is preferably increased during the application of radiation within the absorption spectrum of the photosensitive drug but may be caused instead immediately before or after, such as within two hours.

In the alternative, higher power laser light within the absorption spectrum of the drug causes thermal destruction of tissue which is interactive with the photodynamic effect of the drug. This removes bulky tumors or obstructions by vaporization or vascular occlusion such as by coagulation of blood.

Specific Description of the Drug

In the preferred embodiment, the drug DHE is a water soluble, high molecular weight material derived by treating hematoporphyrin hydrochloride with acetic and sulfuric acids followed by appropriate hydrolysis and filtering to separate the drug based on its large size. Its failure to pass through a filter, such as the MilliPore Pellicon 10,000 molecular weight filter pack, indicates a molecular weight in excess of ten thousand and thus aggregated DHE.

Figure 3:
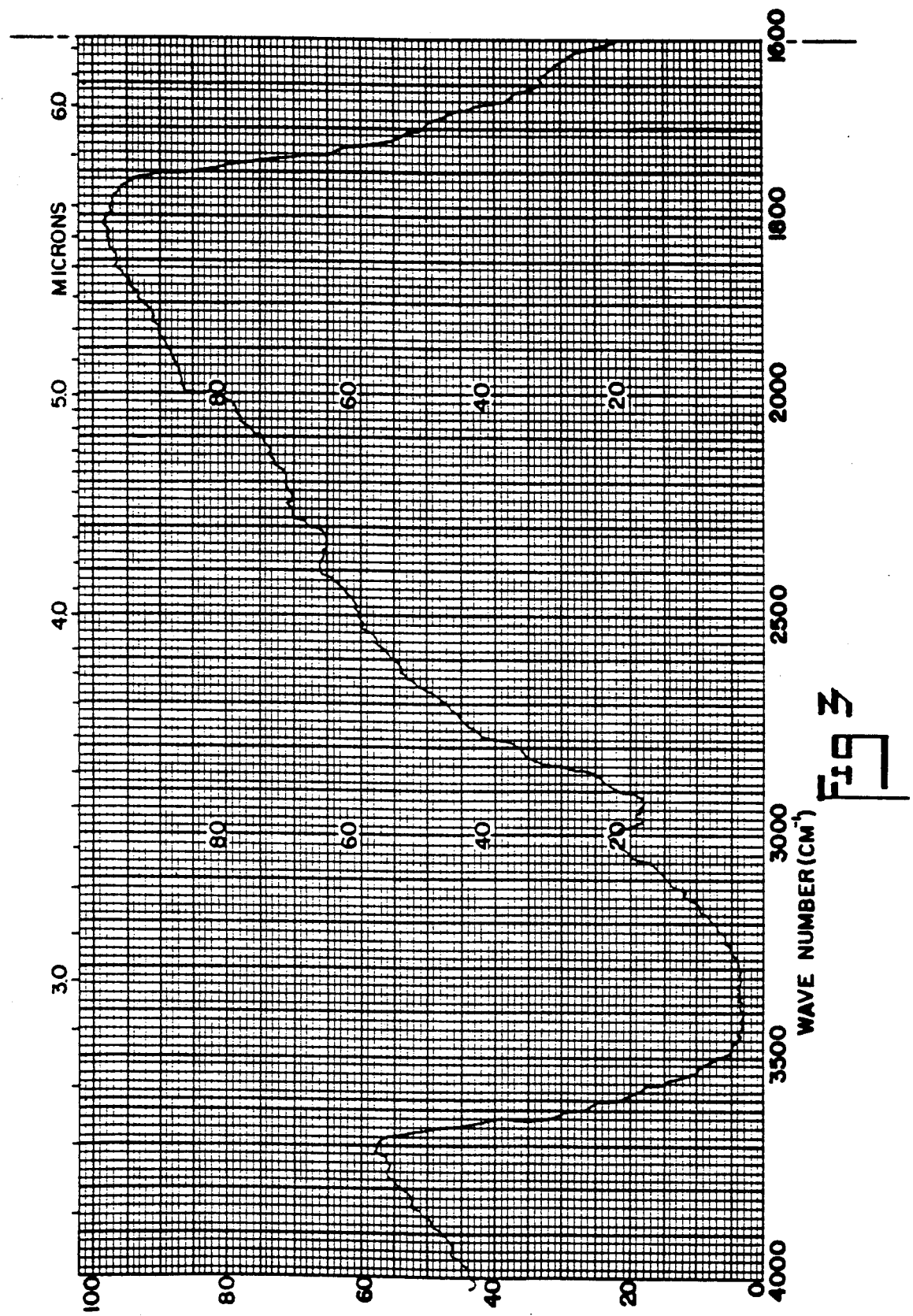
FIGS. 3 and 3A are in combination an infrared spectrum of the drug dispersed in potassium bromide.
Figure 3A:
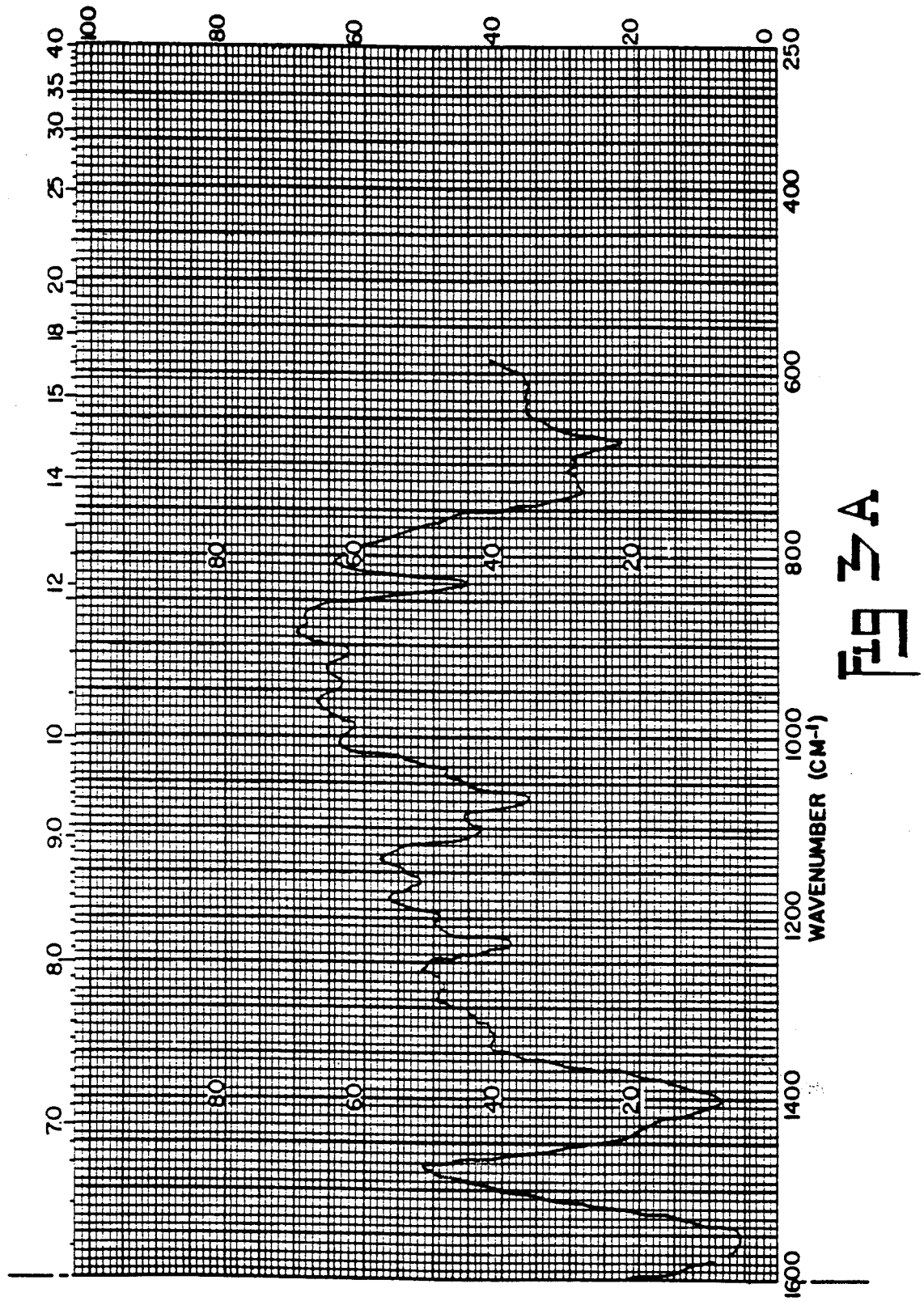

Mass spectrometry of the new drug shows in FIG. 1 especially strong peaks at mass numbes of 149, 219, 591, 609 and characteristic but smaller peaks at 1200, 1218, 1290, 1809. Spectrophotometry of the new orange-red colored drug in aqueous solution reveals in FIG. 2 well-defined peaks at approximately 505, 537, 565 and 615 millimicrons. Infrared spectrophotometry of the new drug dispersed in potassium bromide, reveals in FIG. 3 a broad peak associated with hydrogen stretching, said peak centered at approximately 3.0 microns, and a shoulder at approximately 3.4 microns. Finer peaks are observed at approximately 6.4, 7.1, 8.1, 9.4, 12 and 15 microns.

Elemental analysis of the disodium salt derivative of the new drug shows it to have an empirical formula of $C_{34}H_{35-36}N_4O_{5-6}Na_2$, there being some uncertainty in hydrogen and oxygen due to traces of water which cannot be removed from the drug. A carbon-13 nuclear magnetic resonance study of the drug in completely deuterated dimethylsulfoxide shows in FIG. 4 peaks at approximately 9.0 ppm for $-CH_3$ 18.9 ppm for $-CH_2$, 24.7 ppm for $CH_3$ CHOH, 34.5 ppm for $-CH_2$, 62 ppm for $CH_3$ CHOH, 94.5 ppm for $=C$ (methine), 130–145 ppm for ring C, and 171.7 ppm for $C=O$, all ppm being relative to dimethyl sulfoxide resonance at about 37.5 ppm. Additional vinyl peaks at approximately 118 and 127 ppm may be representative of the new drug or possibly a contaminant.

When the unfiltered reaction product was eluted from a Waters Associates' U Bandpak C-18 column using first, successively methanol, water and acetic acid (20:5:1) and then using tetrahydrofuran and water (4:1), four components were found. Three by-products were identified as hematoporphyrin, hydroxyethylvinyldeuteroporphyrin and protoporphyrin by comparison with standards on thin layer chromatography, with Rf values of approximately 0.19, 0.23, and 0.39 respectively (FIG. 5) using Brinkman SIL silica plates and benzene-methanol-water (60:40:15) as elutent.

Figure 5:
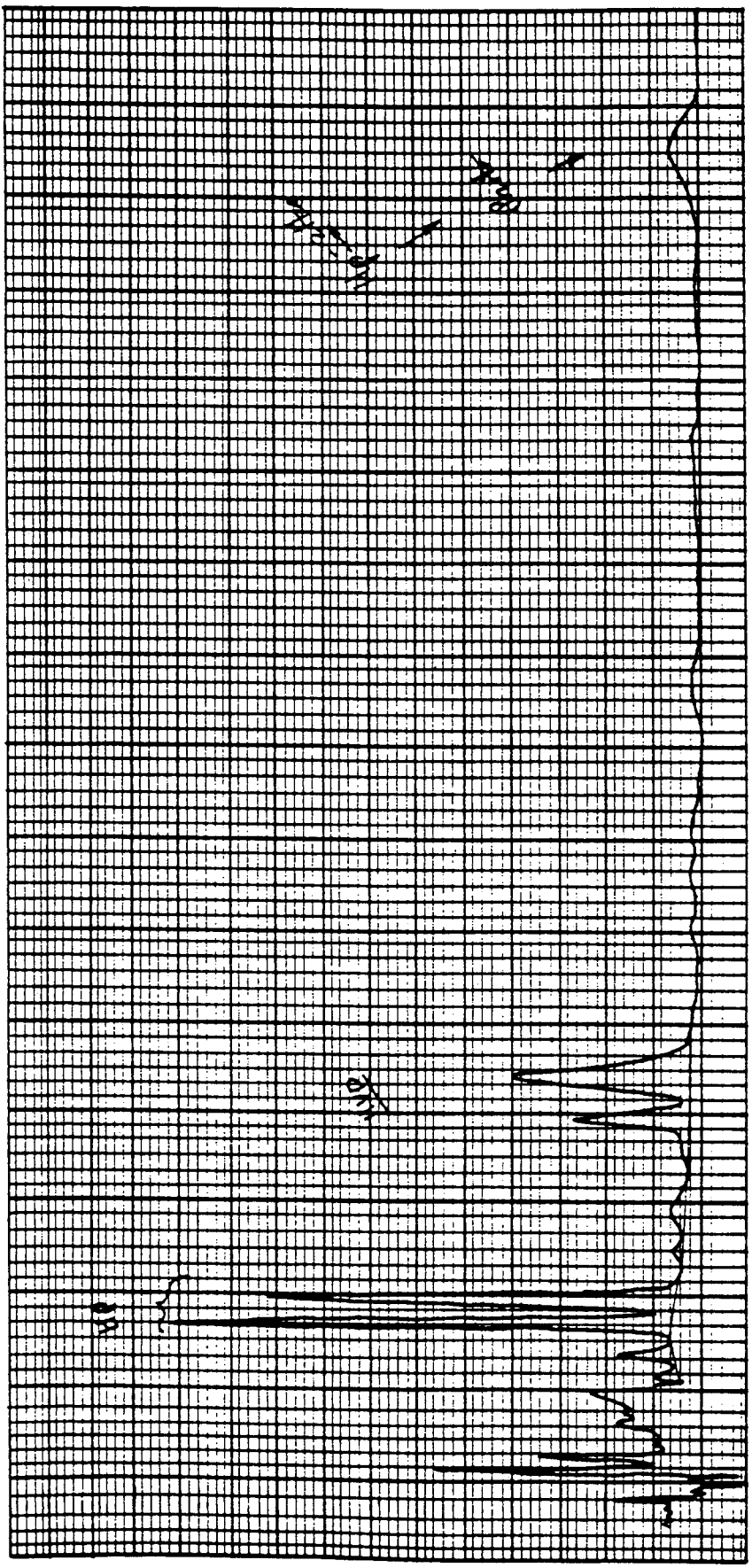
FIGS. 5 and 5A are in combination a print-out from a Waters Associates Variable Wave Length Detector used in conjunction with its U Bondpak C-18 column, showing various components of HpD including a peak formation representative of the drug.
Figure 5A:
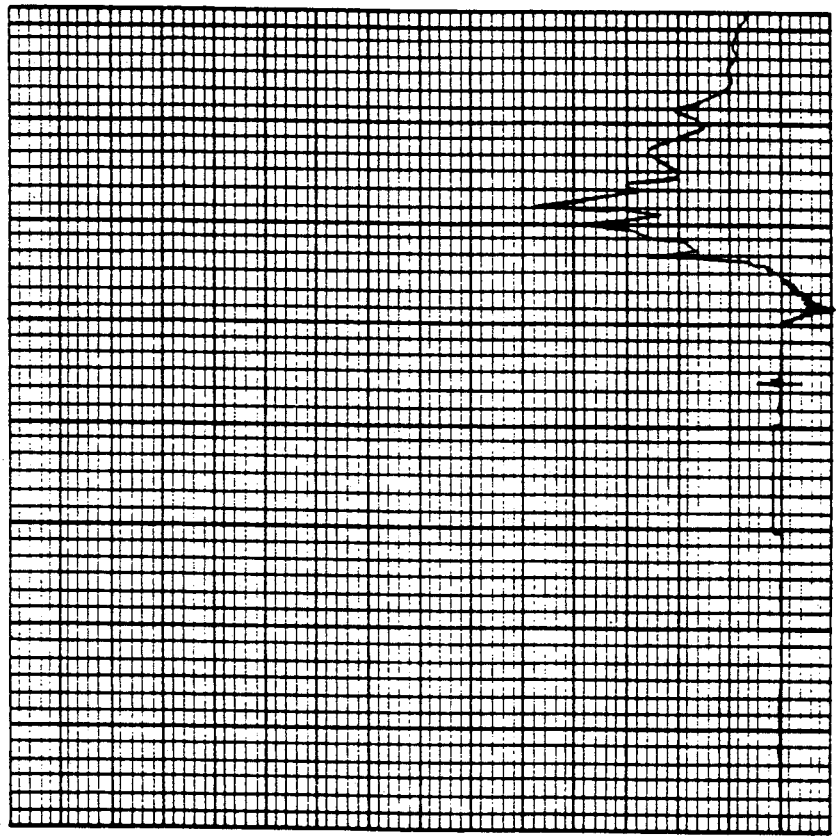
Figure 6:
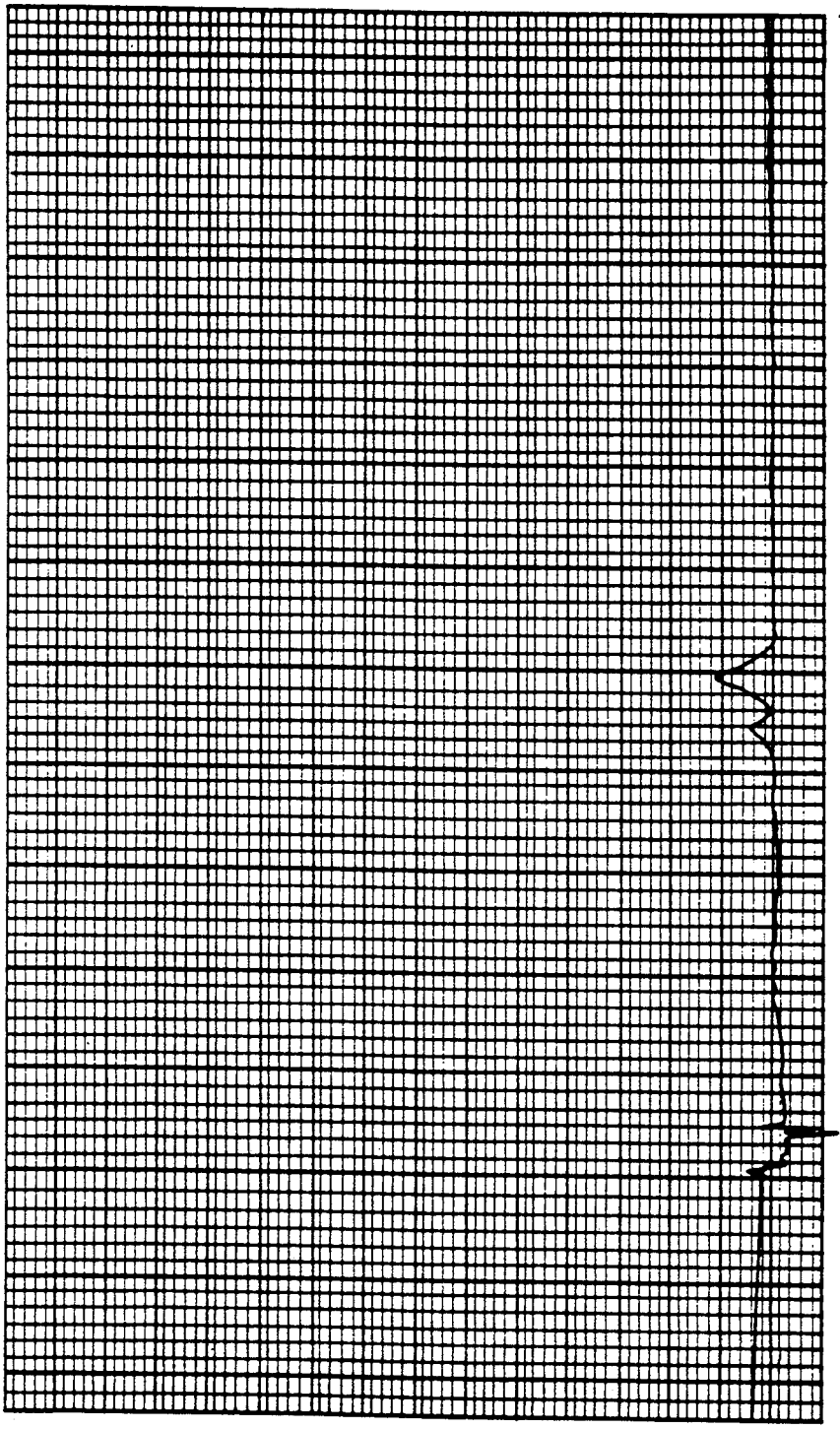
FIGS. 6 and 6A are in combination a print-out from a Waters Associates Variable Wave Length Detector used in conjunction with its U Bondpak C-18 column showing various components of the drug DHE.
Figure 6A:
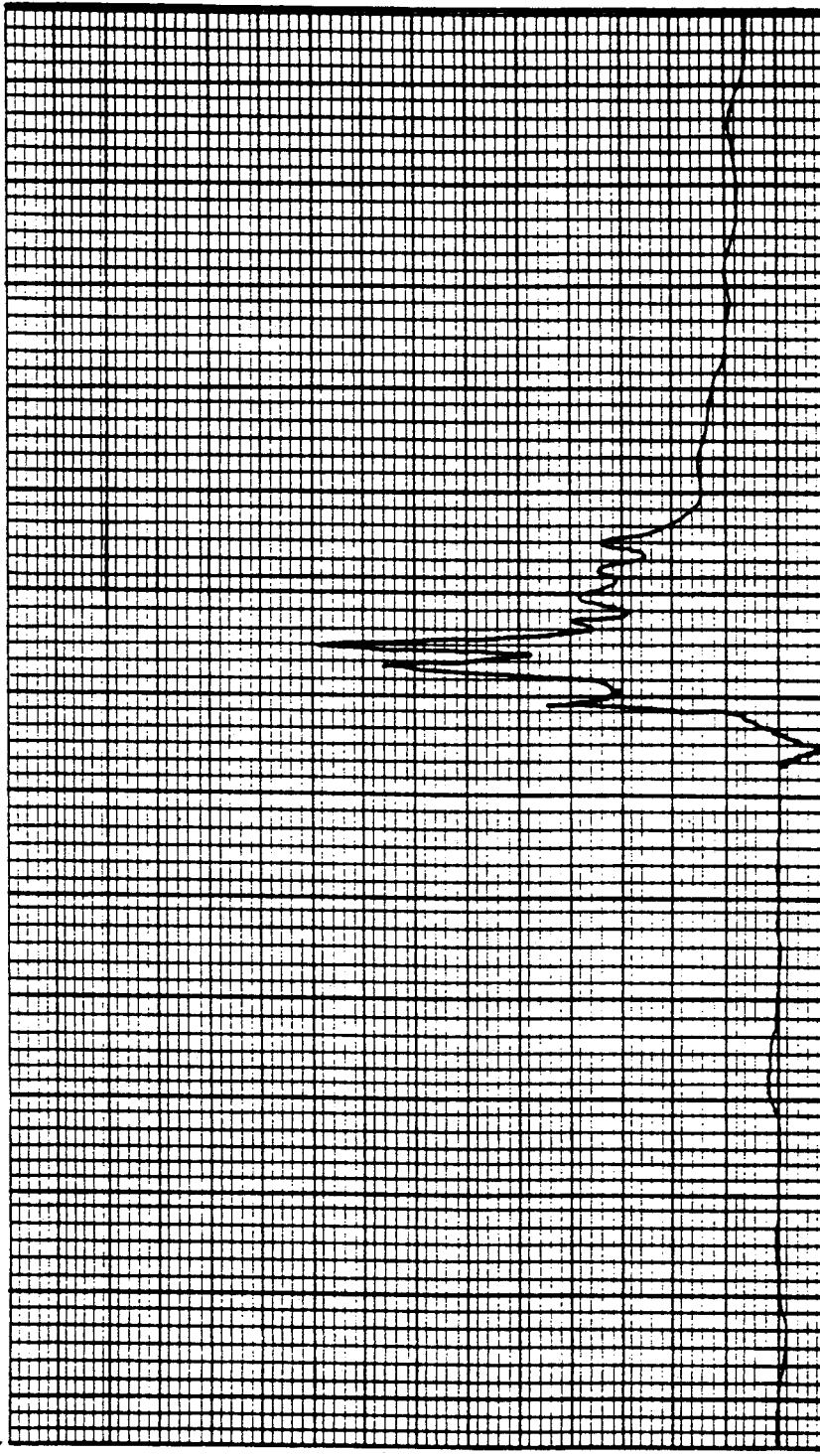

The fourth component shown in FIG. 5 was the biologically active drug of the invention. Chromatography shows in FIG. 6 that exclusion of the above-identified impurities using the MilliPore Pellicon cassette system fitted with a 10,000 molecular weight filter pack, has occurred, during processing of the drug of the invention.

In formula 1, DHE, which is a biologically active drug of this invention, is probably an aggregate of ether molecules formed between two hematoporphyrin molecules by linkage of the hydroxyethylvinyl groups as shown in formula 1. This linkage may occur through hydroxyethylvinyl groups in position 3- or 8- as numbered in formula 1. Linkage may be achieved at position 3- in both halves of the ether, at position 8- in both halves of the ether or through position 3- in one half of the ether and in position 8- in the other half of the ether.

These structures may be named as derivatives of ethyl ether, i.e.: Bis-1-[3-(1-hydroxylethyl) deuteroporphyrin-8-yl] ethyl ether, as shown in formula 1. Other structured isomers may be named: 1-[3-(1-hydroxyethyl) deuteroporphyrin-8-yl]-1'-[8-(1-hydroxyethyl) deuteroporphyrin-3-yl] ethyl ether, or 1-[8-(1-hydroxyethyl) deuteroporphyrin-3-yl]-1'[3-(1-hydroxyethyl) deuteroporphyrin-8-yl] ethyl ether, and Bis-1-[8-(1-hydroxyethyl) deuteroporphyrin-3-yl] ethyl ether.

One or both hydroxyethyl groups at positions 3- or 8-, not used in ether formation, may dehydrate to form vinyl groups. Although experiments have not been conducted, experience indicates that ethers as shown in formula 1 might be substituted with various combinations of hydrogen, alkyl groups, carboxylic acid groups and alcohol-containing groups at various locations of the structure. In addition, many possible optical isomers of these structures exist.

Figure 4:
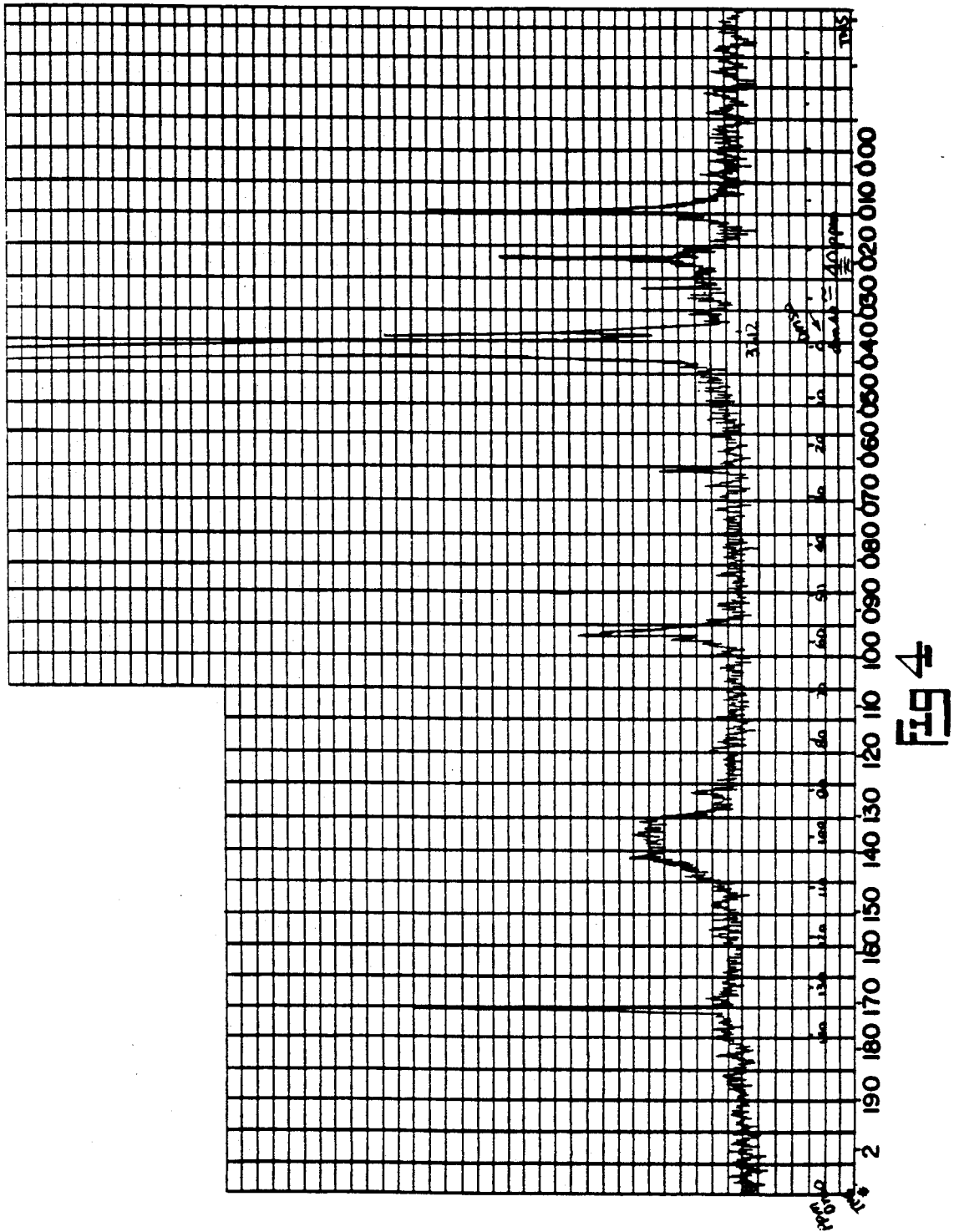
FIG. 4 is a carbon-13 nuclear magnetic resonance print-out of the drug, referenced to dimethyl sulfoxide.
Figure 7:
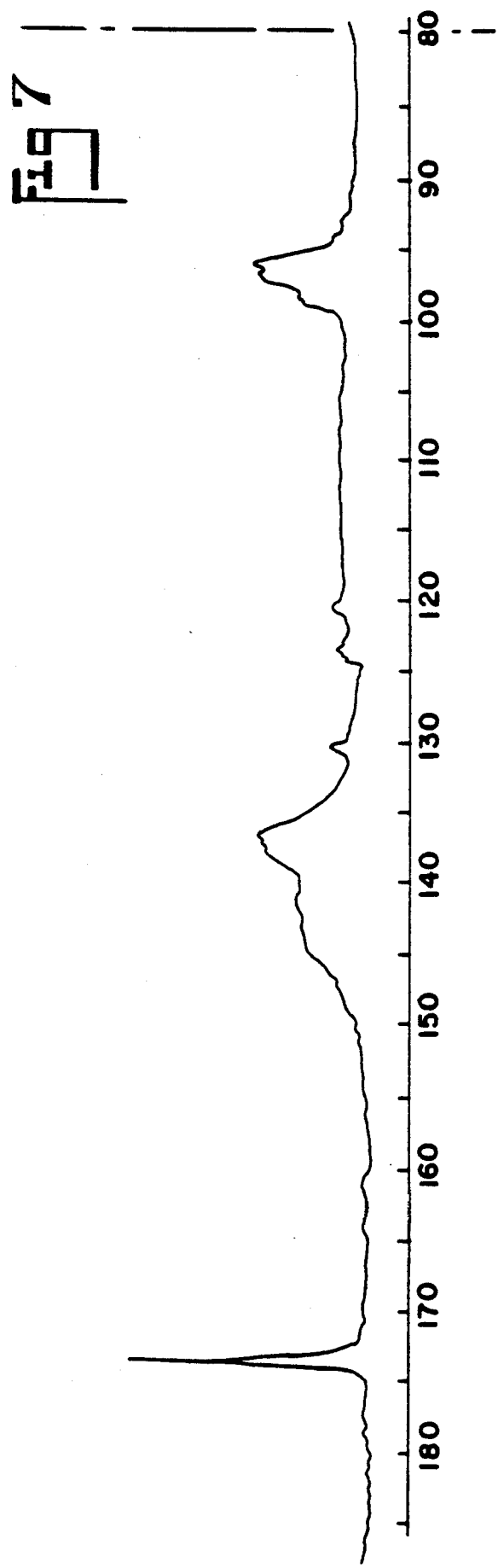
FIG. 7 is a carbon-13 nuclear magnetic resonance print-out of the drug, referenced to tetramethylsilane in deuterated chloroform solvent. Magnification spectrum is shown in the ranges from 20–30 ppm and 55–75 ppm.
Figure 7A:
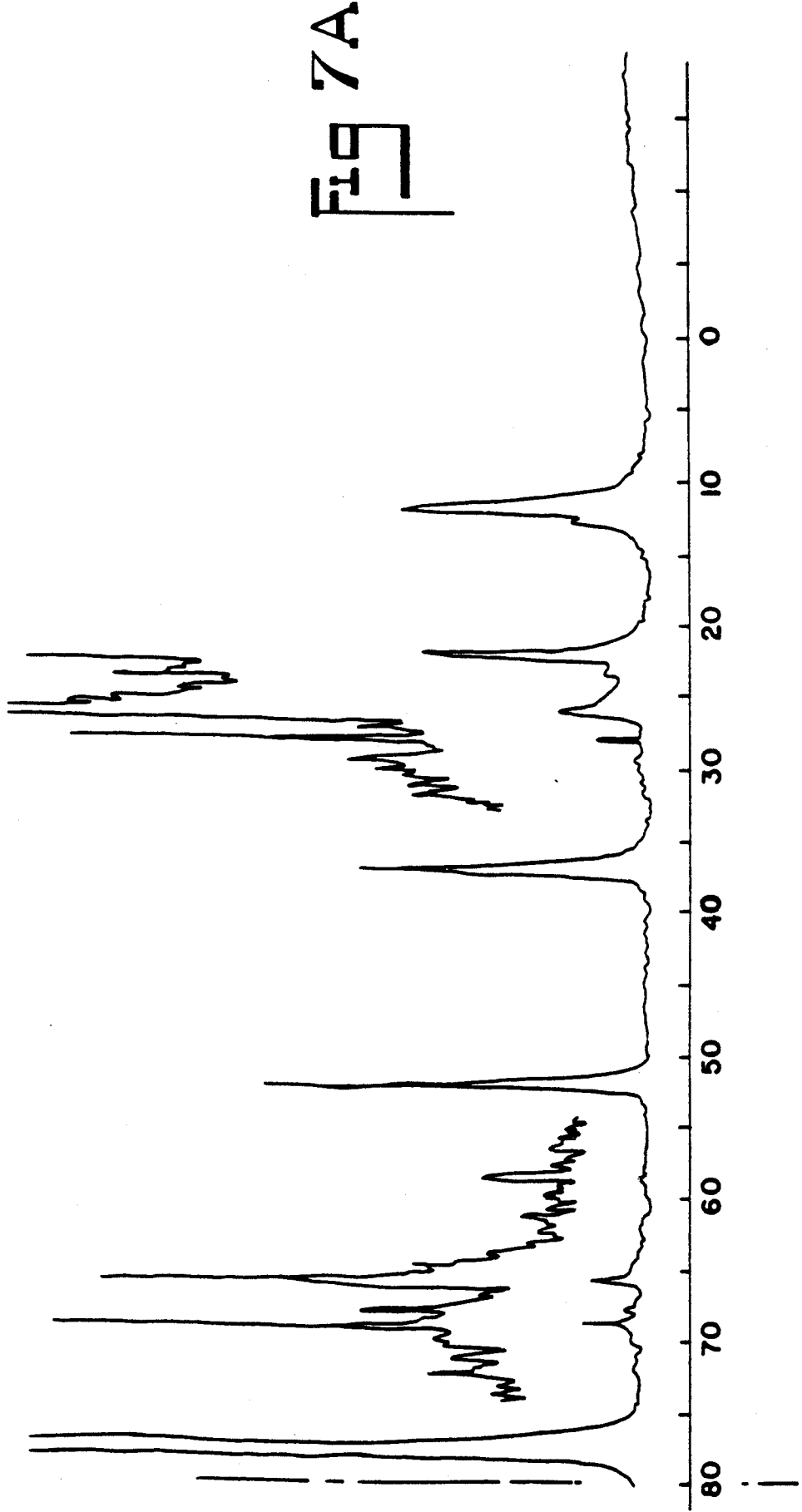

A carbon-13 nuclear magnetic resonance study of the drug in deuterated chloroform referenced to tetramethysilane reveals in FIG. 7 two additional absorbances not previously apparent in FIG. 4. Peaks at 24.7 ppm and 62 ppm in FIG. 4 have shifted to 25.9 ppm and 65.3 ppm respectively in FIG. 7 but newly-developed peaks at 27.9 ppm and 68.4 ppm in FIG. 7 represent resonances for $CH_3$ and H—C—OH bonded from position 3- in FIG. 7, respectively. These newly-developed resonances substantiate the molecular formula depicted in formula 1.

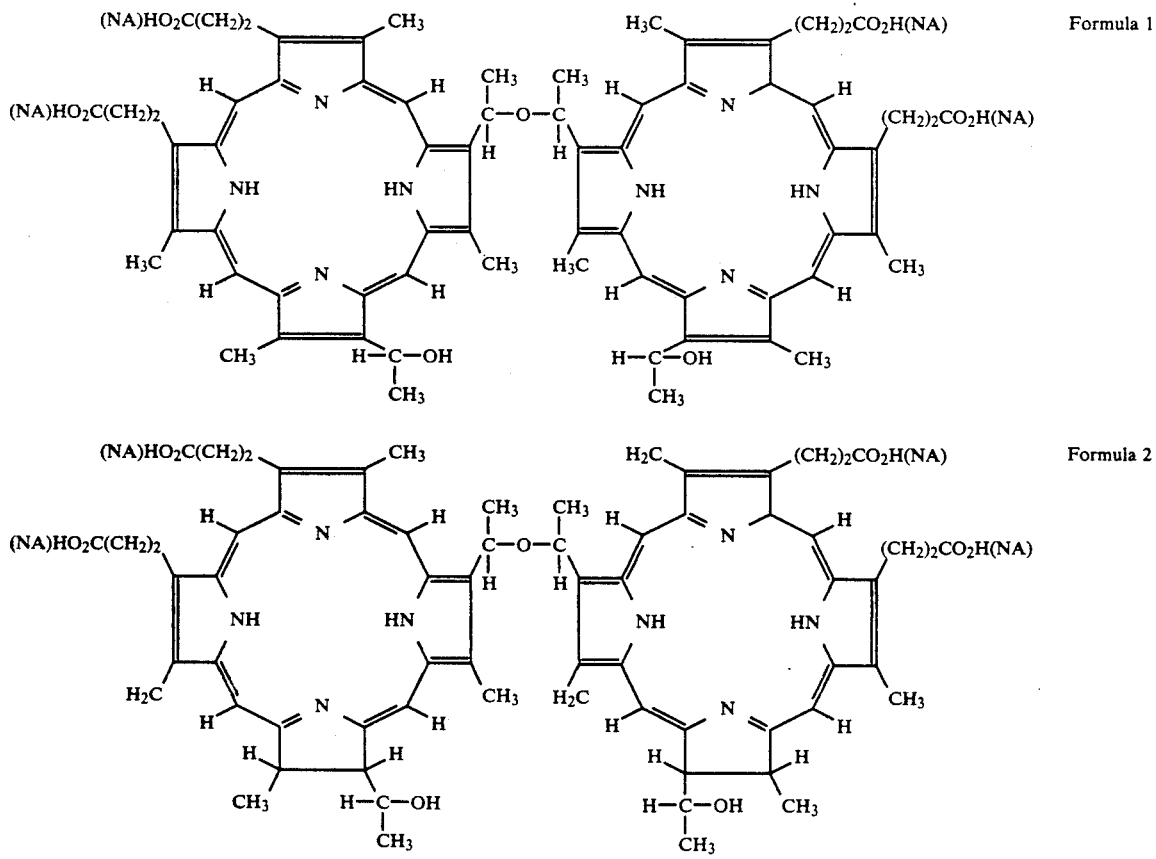

Formula 1

Formula 2

-continued

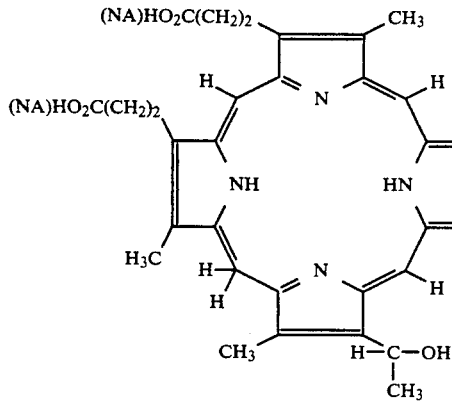 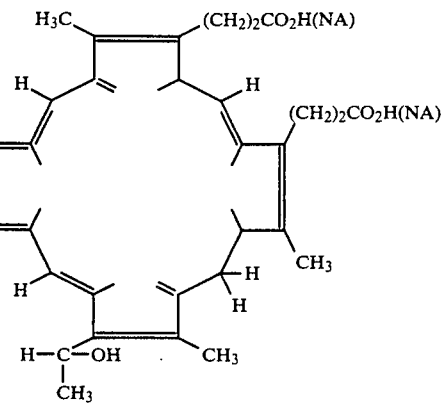

Formula 3

Although DHE is the preferred embodiment, other photosensitizing compounds and delivery systems having the desired ability to enter neoplastic tissue and bind to cells have been prepared and still others are possible. For example, the compound in formula 2, which is a chlorin and the compound in formula 3, which is a phlorin probably will show a response.

A chlorin has been tested and shown to have a response in animals although not as satisfactory as DHE. The exact structure of that chlorin is not known but its spectrum shows it to be a chlorin. This chlorin does not have delivery characteristics because it includes only one chlorin group rather than two groups. Delivery into tumors was accomplished by encapsulating the chlorin in a liposome to enter cells and also by mixing with DHE. The chlorin was bound within the cell, was irradiated and a response observed. For proper delivery, the compounds must either be encapsulated or have two covalently bound groups, each group including four rings forming a larger ring which is the group, some of the rings being pyrroles such as chlorins, phlorins, porphyrins and the like.

. Specific Description of Drug Formation

To prepare one form of a drug from hematoporphyrin, the porphyrin is reacted to form compounds including two porphyrins covalently bound. This reaction is a dehydration reaction to form an ether (DHE) or a condensation reaction for a carbon-carbon linkage which may be possible or any other possible combination of atoms. Moreover, a third linking molecule may be used such as dihaloalykyl compound, which reacts with the hydroxl groups on two porphyrins.

DHE is formed by: (1) lowering the pH of a hematoporphyrin compound to react a hydroxyl group on one of two porphyrins with another porphyrin and thus to form an ether containing the two rings of pyrroles; and (2) removing the DHE formed by this reaction from other moieties.

In another method of forming the ether, a mixture consisting of approximately 20% hematoporphyrin, 50% hematoporphyrin diacetate, 30% hematoporphyrin monoacetate is formed from hematoporphyrin hydrochloride and hydrolyzed. These reactions may be generally expressed by equations 4 and 5, or more specifically by equations 6 and 7 where P is the basic porphyrin group, the peripheral group of which has been acetylated as shown.

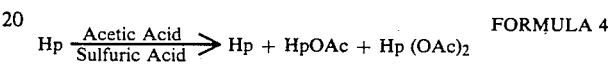

FORMULA 4

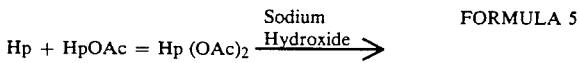

FORMULA 5

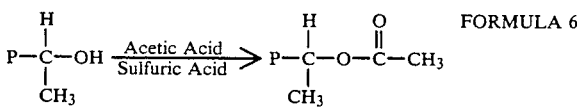

FORMULA 6

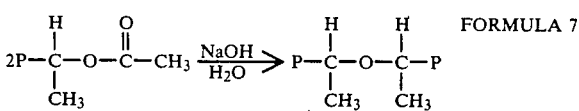

FORMULA 7

This mixture is formed by: (1) adding 285 ml (milliliters) of acetic acid to a 1000 ml Erlenmeyer flask containing Teflon-coated magnetic stirring bar; (2) stirring the acetic acid; (3) slowly adding 15 ml of concentrated sulfuric acid; (4) weighing out 15.0 grams of hematoporphyrin hydrochloride (preferably obtained from Roussel Corporation, Paris, France); (6) adding said hematoporphyrin hydrochloride to the acid solution; and (7) stirring for one hour.

To further the preparation of DHE: (1) a solution of 150 grams of sodium acetate is prepared in 3 liters of glass-distilled water using a 4-liter glass beaker; (2) at the end of one hour, the acetate mixture is filtered, preferably through Whatman No. 1 filter paper, allowing the filtrate to drip into the 4-liter beaker of 5% sodium acetate; (3) the 5% sodium acetate solution now contains a dark red precipitate which is preferably allowed to stand for one hour with occasional stirring; (4) the dark red precipitate is then again filtered, preferably using the above-identified filter mechanism; (5) the filter cake from the filtering process is then washed with glass-distilled water until the filtrate is at pH of 5.5–6.0 (1500–2500 ml of wash water may be required); and (6) the filter cake is then preferably allowed to dry in air at room temperature.

To further purify the DHE, the air-dried precipitate is ground, using for instance, a mortar and pestle until a fine powder is obtained. The powder may then be transferred to a 250 ml round bottom flask. The flask is then attached to a rotating evaporator and rotation under vacuum is maintained at room temperature for preferably 24 hours.

Twenty grams of the vacuum-dried powder is then preferably placed in a 4-liter aspirator bottle which may contain a magnetic stirring bar, and then 1000 ml of 0.1N sodium hydroxide is added thereto. This solution is preferably stirred for one hour and 1.0N hydrochloric acid is then added dropwise until the pH is 9.5.

For the separation of DHE, the aspirator bottle, containing the said solution, is attached to transfer lines leading to a MilliPore Pellicon Cassette system fitted with a 10,000 molecular weight filter pack of the type sold by Millipore Corporation, Bedford, Mass. 01730. The pH of the solution is maintained at 9.5 during this filtration process. It is preferable that the temperature of the solution be ambient. The concentration is increased until the total volume is 400 ml by turning off the feed water and continuing the pump.

The peristallic feed pump is continued and the water feed solution is run through the Pellicon cassette system at a pH of 9.5 and pressure of 10–20 p.s.i.g and maintaining the retentate volume at 400 ml. Pressure may be varied depending on the flow rate through the system.

The filtration process is continued until the retentate solution contains substantially only the high molecular weight, biologically active product. At this time waste monomers are generally no longer present. Exclusion of the waste through the microporous membrane of the filter system is confirmed by analyzing the high molecular weight, biologically active product with a Bio-Gel P-10 column obtainable for example from Bio-Rad, Richmond, Calif. or by high performance liquid chromatography using a Micro-Bondpak C-18 column with fixed variable wavelength detector obtainable for example, from Waters Associates, Milford, Mass.

Concentrations of the product may be increased by running the Pellicon cassette system without water feed. Concentrations of the product may be decreased by adding water. In the preferred embodiment, the concentration of the new drug in solution is approximately 2.5 mg/cc. The pH is adjusted to approximately 7.4 and made isotonic for bottling.

Specific Description of Treatment

The photosensitizing drug is injected into the subject and approximately 3 hours to 2 days is permitted to elapse before applying light. This time may differ in accordance with the patient and treatment but should be adequate to permit the drug to clear normal tissue.

Figure 8:
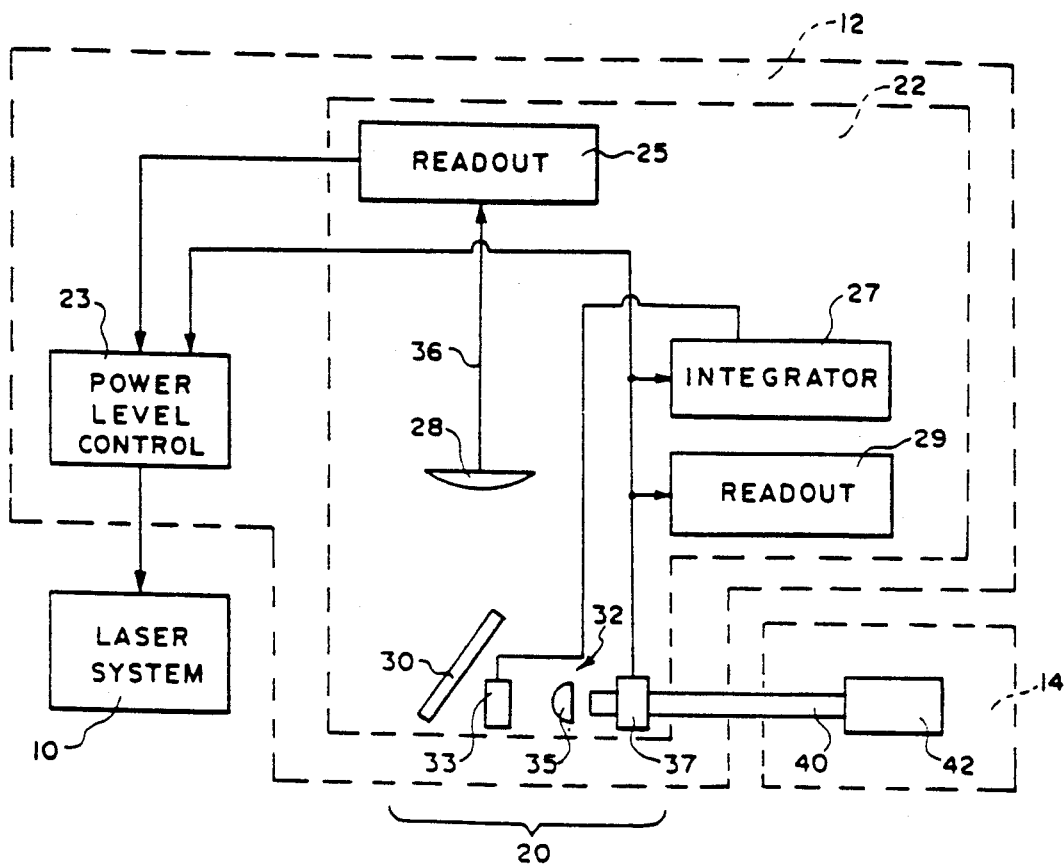
FIG. 8 is a block diagram of a system useful in practicing the invention.

In FIG. 8 there is shown a block diagram of one system for irradiating undesirable tissue having a light source 10 which may be a laser system, a radiation monitor and control system shown generally at 12 and a delivery system shown generally at 14, positioned to radiate a tumor. The light source 10 generally radiates light of the desired frequency and may be a fluorescent lamp system or a laser system of any of several types, such as an argon laser pumping a dye laser, a krypton laser or the like. The light passes through the radiation monitor and control system 12 for delivery through a fiber optic delivery system to a source of undesirable tissue.

The light source 10 includes different configurations such as a single argon laser pumping a dye laser, two parallel sets of argon lasers pumping a dye laser, a krypton laser or a xenon laser. Laser arrangements or other light sources are selected in accordance with the drug and the function. For example, a diagnostic use may call for a different system than a therapeutic treatment of a tumor. The laser system 10 may contain the appropriate means to control frequency, duration and intensity of radiation or the radiation control system 12 may have some or all of such means as part of it. The power applied to the subject should be between 5 milliwatts per square centimeter and $\frac{3}{4}$ of a watt per square centimeter without thermal effects, and with thermal effects, $\frac{1}{4}$ watt to a kilowatt per square centimeter.

The energy application should be at a selected value within the range of from 5 joules per square centimeter to 1,000 joules per square centimeter within a time period for which there is no substantial repair, such as less than two hours. For longer periods, when either intermittent or continuous application is used, more energy may be required.

The radiation monitor and control system 12 includes a light interface system 20, a monitor system 22 and a power level control system 23. The light interface system 20 transmits light from the laser system 10 through the delivery system 14 and transmits signals to the monitor system 22 indicating the intensity of light transmitted to the delivery system 14. It also receives feedback light from the delivery system 14 and transmits a signal representing that light to the monitor system 22. The signals between the monitor system 22 and the light interface system 20 are electrical. A power level control system 23 is connected to the monitor system 22 and to the laser system 10 to control the laser system 10.

The monitor system 22 may have different configurations each with a different complexity. In one arrangement, the manual controls for the laser system 10 are on the monitor and control system 22 such as on the power level control 23 in some of these configurations, feedback signals are applied from the monitor system 22 to the power level control 23 to control intensity and sampling rates for purposes of determining therapeutic effects. The monitor system 22 may include data processing equipment and equipment which displays the results of the laser system 10 and the light interface system 20 on an oscilloscope. The power level control 23 may be considered part of the laser system by some manufacturers but is discussed separately here for convenience.

The light interface system 20 includes an optical interface and a sensor 28. The optical interface and the sensor 28 are enclosed within a cabinet for the shielding of light and electrical conductors 36 connect the sensor 28 to the monitor system 22.

To transmit light from the laser system 10 to the delivery system 14, the optical interface includes a beam splitter 30 and a lens system 32 having a shutter 33 and a lens 35. The beam splitter 30 passes light from the laser system 10 to the lens system 32 for transmission through the delivery system 14 to the spot of therapy and to the sensor 28 for detection. Light is transmitted through the delivery system 14 to a leakage detector at 37 which includes a light sensor electrically connected to the monitor system 22 and the power level control system 23.

The delivery system 14 includes light conductors 40 and a light transmission unit 42 connected together so that the light conductors 40 receive light from the lens system 32. There may optionally be included other types of equipment such has an endoscope.

To monitor the therapy, the monitor system 22 includes a readout system 25, an integrator 27 and a readout system 29. The light sensor 28 applies signals to the readout system 25 which, in one embodiment, uses the signals to control the power level control 23 in accordance with light from the beam splitter 30 indicating laser output to the fibers 40 from the laser system 10. The readout 25 also provides a visible readout indicating power output from the laser system 10 as well as providing signals to the power level control 23.

The leakage detector 37 applies signals to the readout 29, integrator 27 and power level control 23. This signal can be used to calibrate the output from the delivery system 14 since it indicates loss in the delivery system. This loss is a constant fraction of delivered light. The delivery system is calibrated by measuring its output in an integrating sphere in a manner known in the art and correlating it with the output from detector 37. With the relationship between leakage and output power known, a reliable feedback for monitoring and control is obtained which relates to power being transmitted through the light conductor to the subject thus compensating for coupling losses to the light conductor. The shutter 33 is controlled by the integrator 27 to control the power dosage by blocking light to the delivery system 14 when the integrated power or energy reaches a predetermined dosage set into the integrator 27.

The delivery system is intended to: (1) deliver the light in close proximity to the neoplastic tissue that is to be observed or destroyed: (2) have sufficiently low attenuation to permit an adequate intensity of light; (3) transmit received luminescent light and feedback signals and the like useful in observation and control; (4) be able to be inserted into locations propitious for irradiating light at the desired location; (5) be capable of directing light in an appropriate pattern; (6) be sufficiently strong to avoid breaking off of parts in use; (7) have sufficient capability to resist deterioration from the heat it handles; and (8) incorporates materials with low absorption at the frequencies used in treatment so as to reduce heating.

Figure 9:
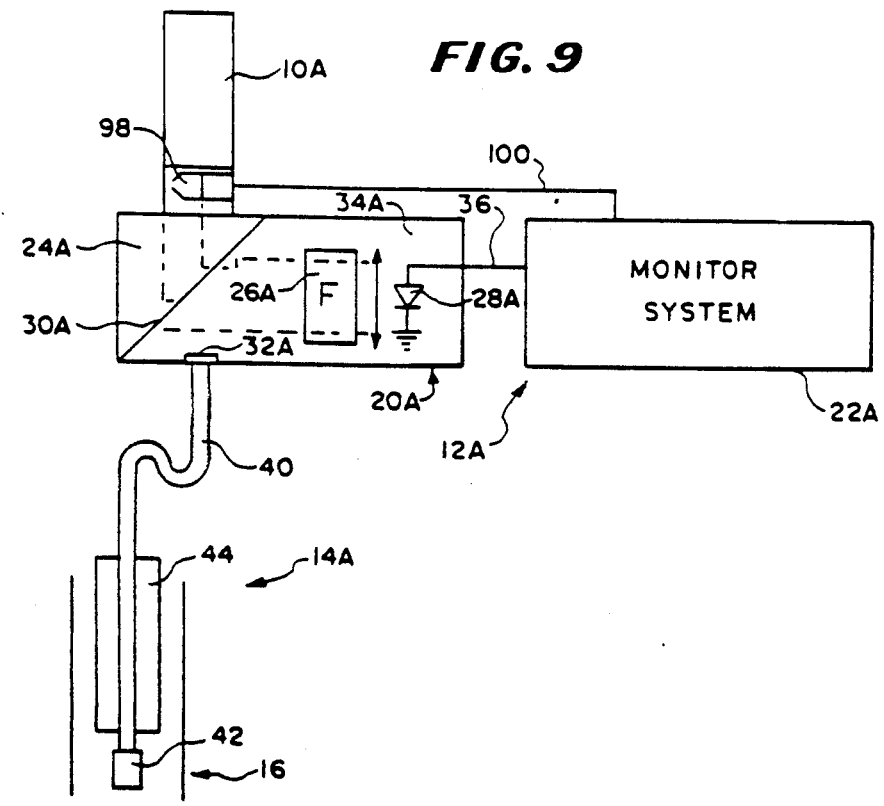
FIG. 9 is a block diagram of another system useful in practicing the invention.

In FIG. 9 there is shown a block diagram of a combination of radiation monitor and treatment system having a laser system 10A, a monitoring and radiation control system shown generally at 12A and a delivery system shown generally at 14A, positioned to radiate a tumor on a bronchial wall 16A of a subject. The laser system 10A generally radiates light of the desired frequency through the monitoring and radiation control system 12A for delivery through a fiber optic delivery system to the cancer on the bronchial wall 16A.

The monitoring and radiation control system 12A includes a light interface system 20A and a monitor system 22A. The light interface system 20A transmits light from the laser system 10A through the delivery system 14A and transmits signals to the monitor system 22A indicating the intensity of light transmitted to the delivery system 14A. It also receives feedback light from the delivery system 14A and transmits a signal representing that light to the monitor system 22A. The signals between the monitor system 22A and the light interface system 20A are electrical.

The light interface system 20A includes an optical interface 24A, a filter 26A and a sensor 28A. The optical interface 24A, the filter 26A and the sensor 28A are enclosed within a cabinet 34A for the shielding of light with electrical conductors 36A connecting the sensor 28A to the monitor system 22A.

To transmit light from the laser system 10A to the delivery system 14A, the optical interface 24A includes a mirror 30A and a lens system 32A. The mirror 30A includes a central aperture which passes light from the laser system 10A to the lens system 32A for transmission through the delivery system 14A to the spot of therapy. Light is transmitted through the delivery system 14A from the spot of therapy back to the lens system 32A for transmission to the filter 26A.

The delivery system 14A includes a plurality of light conductors 40A and a light transmission unit 42A connected together so that the light conductors 40A receive light from the lens system 32A, originating with the laser system 10A, and transmit light from a luminescent surface such as neoplastic tissue containing photosensitive drug back to the lens system 32A for transmission to the filter 26A. There may optionally be included other types of equipment such as an endoscope 44A.

To monitor the therapy, the filter 26A is positioned between the mirror 30A and the sensor 28A to pass a narrow band of frequencies to the sensor 29A which converts the light to an electrical signal for transmission through the conductor 36A to the monitor system 22A. The mirror is positioned such that light from the delivery system 14A passing through the lens system 32A is reflected by the mirror 30A through the filter 26A to the sensor 28A.

The light leaving the delivery system 14A from the tumor is in a cone that radiates over an area of the mirror 30A while the mirror 30A has light from the laser system 10A forming a beam through the small central aperture therein onto the lens 32A for transmission through a fiber of the light conductor bundle 40 onto the tumor. The signals from the detector 29A may indicate the amount of illumination or the location of illumination or the generation of triplet state oxygen indicating destruction of neoplastic tissue and thus may be used for locating tumors or for indicating the amount of photodynamic derstruction of neoplastic tissue.

To reduce noise, the monitor 22A controls a chopper 98 to chop light at a suitable frequency such as 90 hz (hertz) which can be detected in the monitor system 22A by synchronous demodulation. This is controlled by a signal on conductor 100 which originates from the chopper drive voltage. This frequency is low enough so that the half life of the fluorescence of the drug is much smaller than a half cycle of the chopper so as not to be blocked. The frequency of chopping is selected to block ambient noise from room lamp sources and to reduce drift. Moreover, in the preferred embodiment, the light transmitted through the delivery system is 630 nm so as to be distinguished from 690 nm fluorescence from the drug.

Although a delivery system 14A has been described which is suitable for treatment of a tumor on a bronchial wall, other types of delivery systems are known which transmit light for such use and other configurations of delivery systems are available for other types of therapy such as for bladder or the like.

Figure 10:
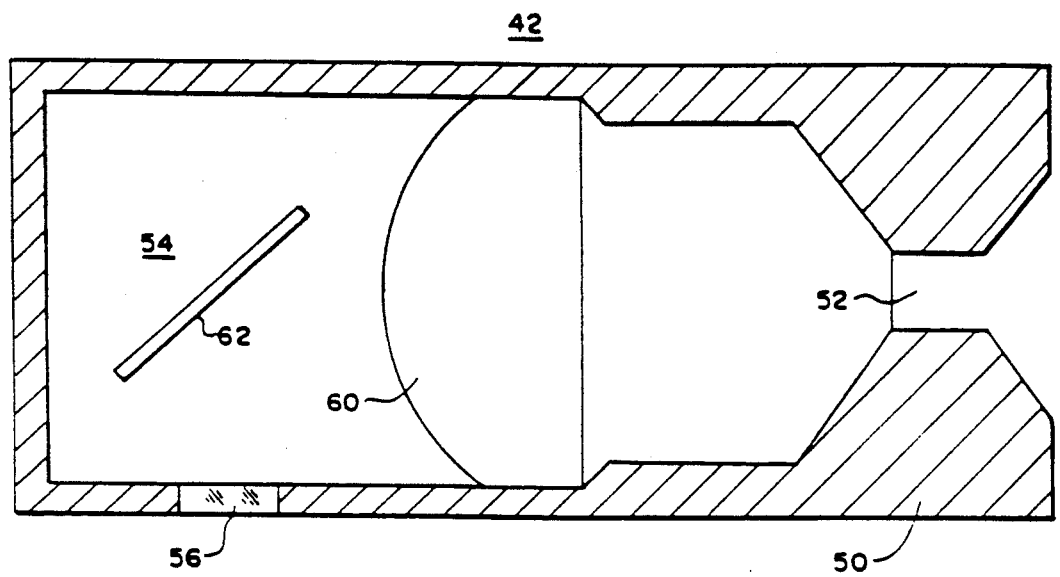
FIG. 10 is a simplified enlarged longitudinal sectional view of a portion of the system of FIG. 9.

In FIG. 10 there is shown a sectional view of a transmission unit 42 for treating or locating a spot on a bronchial wall having a generally cylindrical shaped opaque casing 50, a fiber optic connecting socket 52 and an image control section 54. The opaque casing 50 is sealed and contains in one end, the fiber optic connecting socket 52 which is funnel-shaped for receiving the ends of the fiber optic light conductors into the hollow interior of the opaque casing 50. The light conductors are sealed in place by any suitable means such as by adhesive, molding, threading, swaging or the like.

The image control section 54 is fitted within the housing in communication with the fiber optic conductors to focus light from the fiber optic bundle in a fixed configuration through a light-passing window 56 in the opaque casing 50 onto a spot to be treated and to reflect fluorescent light passing through the window 56 from tissue back to the ends of the fiber optic conductors in the fiber optic connecting socket 52.

The image control section 54 includes one or more lens 60 and one or more mirrors 62. The lens 60 and mirrors 62 are positioned with respect to the aperture 56 so that light from the lens 60 focuses an image of the ends of the fiber optic conductors in the connecting socket 52 onto the mirror 62 which reflects that image through the aperture 56. The mirror also receives fluorescence and exciting light at fixed distances from the light passing through the aperture 56 from the ends of the fiber optic connecting socket 52 back through the lens 60 onto light conductors as a feedback signal. In the preferred embodiment, there are three apertures to measure the attenuation coefficient of tissue, three mirrors, three lens and three light conductors forming three light paths, aligned with each other.

Figure 11:
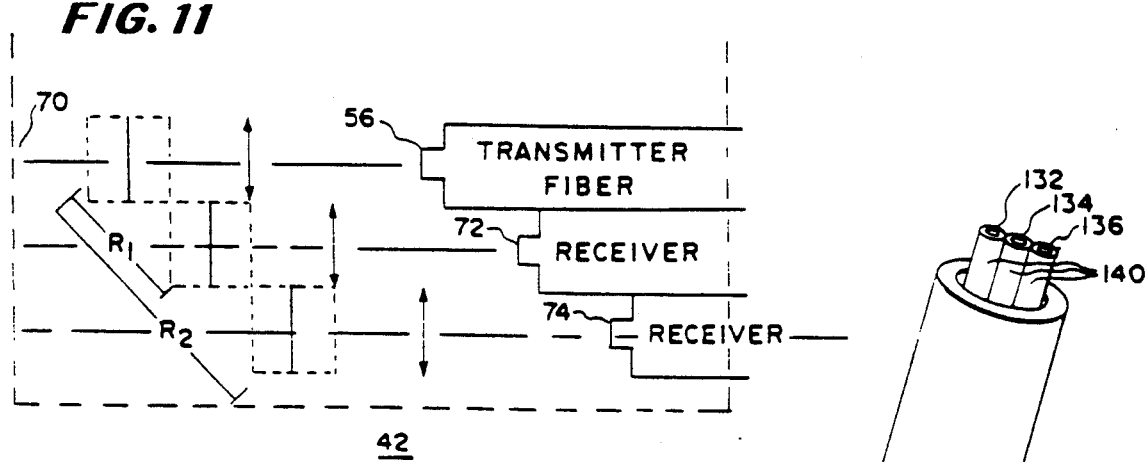
FIG. 11 is a developed view of the portion of the system of FIG. 8 that is shown in FIG. 10.

In FIG. 11 there is shown a developed view of a transmission unit 42 having three apertures, lens, windows, mirrors and light conductors. The first or end aperture 56 transmits light to a surface indicated at 70 and two light receiver apertures are positioned side by side with the transmitting aperture 56 at 72 and 74 spaced from each other by distances R1 and R2 so that the receiver aperture 74 receives light at a distance R2 from the transmitted light and the receiver 72 receives light at a distance R1. The receivers are used because the light received by a receiver yields information concerning: (1) total attenuation coefficient of the tissue at the exciting frequency; (2) drug levels at certain fluorescent frequencies; and (3) the effectiveness of treatment of tissue at certain other fluorescent wavelengths.

Moreover, it has been discovered that fiber conductors against the surface of the tissue are able to receive a signal from the tissue without penetration of surface which represents the light diffused through the surface. The measurement of this light can be used for dosemetry as described for the reading head 42 of FIG. 10 and the explanation of FIG. 11 applies equally to such receivers.

Firstly, the measurement of light at the wavelength emitted by the drug in tissue provides a measure of the drug concentration. Secondly, the measurement of light at the incident wavelength without drug in the tissue at points spaced from the location incident on the tissue provides a measure of the attenuation constant and thus the penetration for certain intensities. Thirdly, the measurement of certain frequencies at times related to energization of the drug and oxygen provides signals related to destruction of undesirable tissue.

The amount of certain frequencies of emitted light is related to the destruction of tissue and thus to the intensity of applied radiation, the attenuation constant in the tissue, the amount of drug, the availability of oxygen and the distance from the incident radiation. Measurement of this radiation provides a general indication of activity. The fluorescent irradiance is linearly related to drug concentration with a known exciting irradiance so that a measure of drug concentration is obtainable after calibration. From this relationship the clearance of drug from tissue can be determined after injection and during periodic light treatment.

The depth of penetration of an adequate exciting radiation into tumor can be estimated from the attenuation coefficient of tissue and the irradiance output increased to the value necessary for the selected depth chosen. The attenuation coefficient can be measured by biopsy or from a measurement of the irradiance at the exciting frequency at a first and second location from the incident exciting radiation.

This coefficient is equal to the product of two factors. The first factor is the reciprocal of the difference between the distance from the incident radiation to the first point and the distance from the incident radiation to the second point. The distances are both within the tissue. The second factor is the natural log of a fraction having a numerator and a denominator. The numerator is the product of the measured irradiance at the seond point and the distance between the incident irradiation and the second point. The denominator is the product of the irradiance at the first point and the distance between the incident exciting radiation and the first point.

Figure 12:
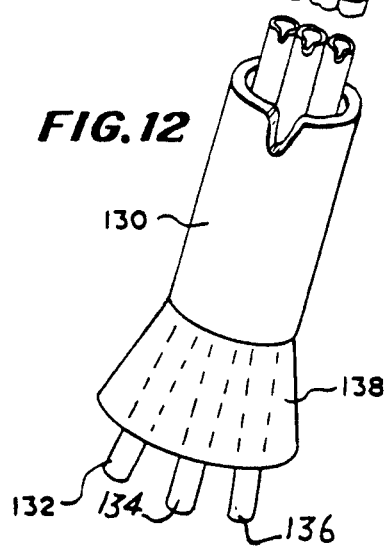
FIG. 12 is a simplified perspective view partly broken away of another embodiment of a portion of FIG. 9.

One type of apparatus for measuring the coefficient of attenuation is shown in FIG. 12 having a outer sheath 130, a transmitting light conductor 132, a first light receiving conductor 134, a second light receiving conductor 136 and a spacing wedge 138. This apparatus is shown broken away at 140 to illustrate that it may be longer than actually shown.

To measure the irradiance at the first and second points for calculation of the coefficient, the outer sheath 130 slidably confines the light conductors 132, 134 and 136. It is sized to be inserted to the tissue being measured and to accommodate the transmission of light to the tissue through conductor 132 and the measurement of irradiance through conductors 134 and 136. It may be inserted through an endoscope until the conductors 132, 134 and 136 contact the tissue.

To measure the distance between the incident radiation from conductor 132 and the first and second point at conductors 134 and 136 for calculating the coefficient of attenuation, the conductors are spaced at fixed angles to each other in a line by sheath 138 so that the distance between their ends can be trigonometrically calculated from the angle and the amount they are extended from the apex of the triangle. The angles of the conductors are 30 degrees between conductors 132 and 134 and 60 degrees between conductors 132 and 136. The lengths extended are measured by marks such as those shown at 140 on conductor 136 compared to the edge of the sheath 138.

Of course, the distance may be fixed, but the embodiment of FIG. 12 provides an adjustable device that may select different distances and be used for different tissue locations. The light conductors may be withdrawn for protection during insertion. With the attenuation constant known, the depth of penetration of a minimum irradiance or conversely the required irradiance for a minimum intensity at a given distance may be calculated. The calculations are based on one of three expressions.

In the first expression, the light is emitted from a source that is substantially a point source and the expression provides the treatment distance to a point of an assumed light flux density. In this expression, the length of treatment in tissue is the total length through the tissue from the point source in any direction through the treatment distance from the point source. Thus, the length of treatment through tissue or along any straight line through the point source extends for a length equal to twice the treatment distance in this expression. It will cover a sphere or a section of a sphere having a radius equal to this distance.

In this first expression, the assumed minimum irradiance is equal to the irradiance at the point source divided by a denominator which is a product of two factors: the first being the distance from the point source to the point of assumed minimum irradiance and the second being the natural log base raised to the power of the product of the distance and the attenuation coefficient. The attenuation coefficient is a number characteristic of the tissue and has the dimensions of the reciprocal of length. It is the reciprocal of the distance at which the irradiance is reduced by a factor of one divided by the natural log base.

In the second expression, the light is incident on the surface as an approximate plane wave. In this expression, the distance of treatment is perpendicular to surface to a depth of the assumed necessary minimum irradiance. The minimum irradiance across the treatment distance is equal to a fraction having a numerator and denominator. The numerator is the irradiance at the surface and the denominator is the natural log base raised to the power of the product of the maximum treatment distance and the attenuation coefficient.

In the third expression, the light emitter is a cylinder embedded in the tissue and the space irradiance varies as the modified Bessel function of the second kind of the 0 order, which decreases more slowly with distance than does the function for a point source described above in expression one.

Figure 13:
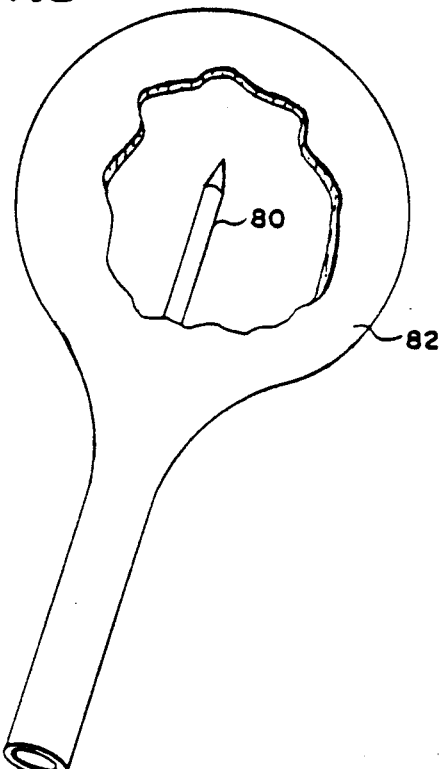
FIG. 13 is a perspective view partly broken away of another embodiment of a portion of the system of FIG. 9.

In FIG. 13 there is shown a bulb-type light-emitting source 42A having a light transmission fiber 80 inserted in a diffusing bulb 82 which receives light, diffuses it within the bulb and emits it with equal intensity in all directions. This bulb may be used to irradiate a large area such as a bladder or the like.

Figure 14:
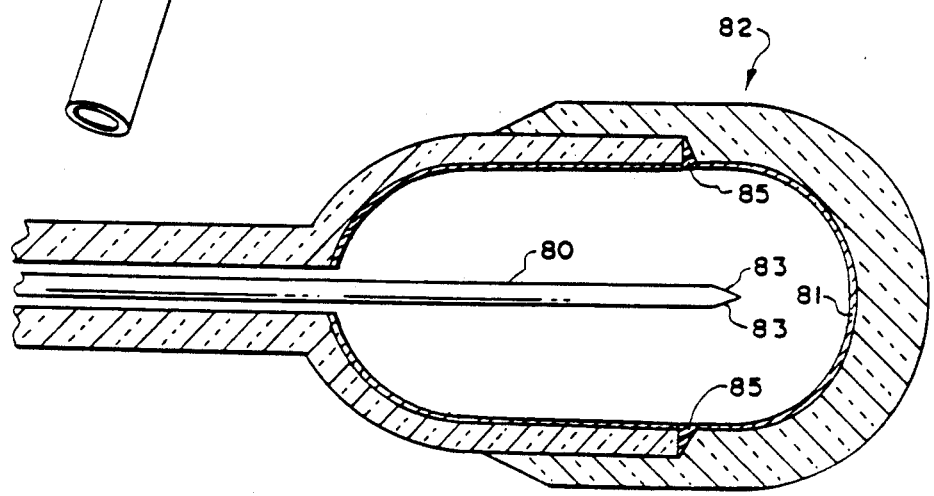
FIG. 14 is a longitudinal sectional view of the embodiment of FIG. 12.

In FIG. 14 there is shown a sectional view of the light-emitting source 42A having the light fiber 80 inserted into the diffusing bulb 82. The diffusing bulb 82 is polycarbonate, held in place by epoxy glue 85 and capable of transmitting light therethrough from ground surfaces 83 on the ends of the light conductor 80. Alternatively, the surfaces 83 may be fused as half a sphere to control the angle of irradiation or other lenses may be used. Its inner surface is coated with a reflective diffusing material 87, which in the preferred embodiment is formed of particles of saphire united by epoxy to the inner surface to reflect light within the diffusing bulb 82. However, it may be other reflective materials such as barium sulfate. Light is also forward scattered and emitted.

The diffusing bulb 82 is fluid tight, of sufficient size to avoid, during normal use, a temperature increase so great at any location as to degrade the material to the point of breaking. It is usually submerged in a fluid or semifluid matter and at a distance so the power density is low at the first surface that absorbs light. Thus, this surface in contact with blood receives light having an optical power density low enough so that it remains relatively cool and blood does not coagulate on it.

Figure 15:
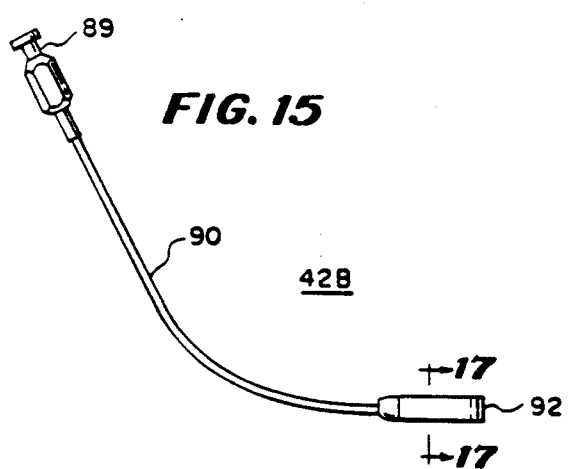
FIG. 15 is an elevational view of still another embodiment of a portion of the system of FIG. 9.

In FIG. 15 there is shown a side elevational view of an eye applicator 42B, having a hollow tubular stem 90 for receiving a fiber conductor and a reflector 92 positioned to receive light from the fiber conductor and reflect it onto a particular tumor. The hollow tubular stem 90 is relatively stiff and "L" shaped with a plastic cylindrical socket 89 on one end and the reflector 92 on the other end so that the reflector 92 may be inserted behind the eye with the socket 89 outside the eye to receive a light conductor.

Figure 16:
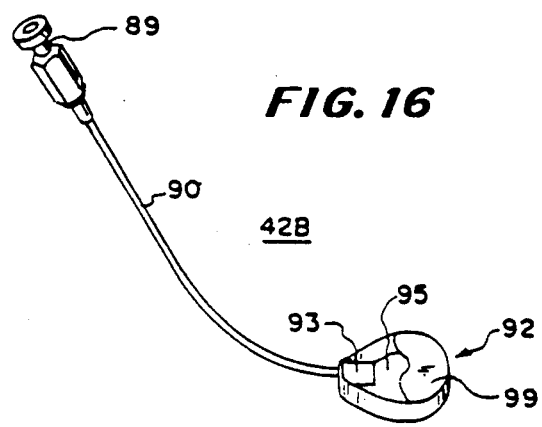
FIG. 16 is a perspective view partly broken away of the embodiment of FIG. 14.

As best shown in FIG. 16, the socket 89 is tubular to receive and hold a light conductor so that light may be conducted through the hollow tubular stem 90 to an aperture 93 where the stem 90 joins the reflector 92. The stem 90 is less than one eighth inch in diameter. The reflector 92 includes a cylindrical reflective portion 95 covered by a transparent diffusing surface 97.

Figure 17:
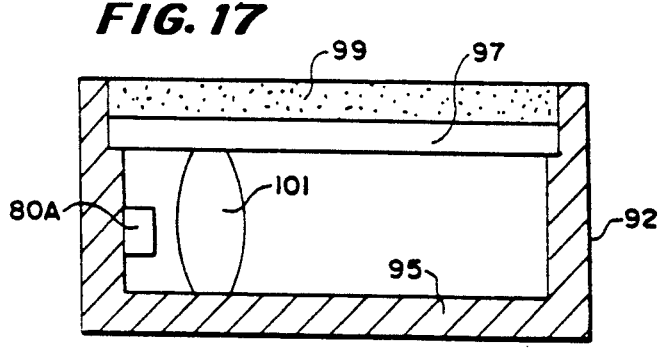
FIG. 17 is a sectional view of a portion of the embodiment of FIG. 14.

As shown in FIG. 17, the reflector 92 is cap-shaped with a polished reflective surface curved to reflect light it receives from the light conductor 80A in multiple paths to obtain an even distribution. The light passes through a 400 micron light conductor 80A in the stem 90 (FIGS. 15 and 16) and a 600 micron diameter quartz cylindrical lens 101 that transmits light in paths parallel to the open end of the reflector 92 through a wider angle than paths toward the open end. This increases multiple path reflections and even distribution of the light across the selected area, thus reducing spot intensity and covering an area.

The open end of the reflector 92 is either: (1) on the side closest to the socket 89; or (2) furthest from a reflective back 95. It functions to direct light into the eye or away from the eye onto optic nerves. In the former case, the open end is covered with the diffusing surface 99 parallel to and aligned with the open end of the reflector 92 to diffuse light. The open end is sealed by a light passing member 95. In the latter case, the open end faces in the opposite direction and is also sealed by a light passing member.

Figure 18:
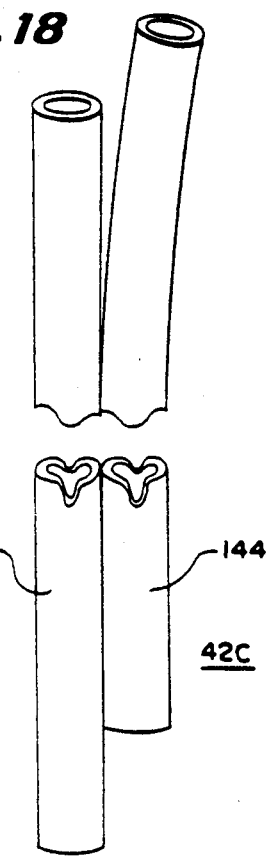
FIG. 18 is a perspective simplified view, partly broken away of another embodiment of a portion of FIG. 8.

In FIG. 18, there is shown still another light emitting source 42C having an emitting light conductor 144 and a receiving conductor 142. In this embodiment, the receiving light conductor fits against the surface to receive radiation within the tissue and spaces the emitting conductor 144 to which it is attached from the surface of the tissue by a selected distance to irradiate a selected surface area of the tissue.

Figure 19:
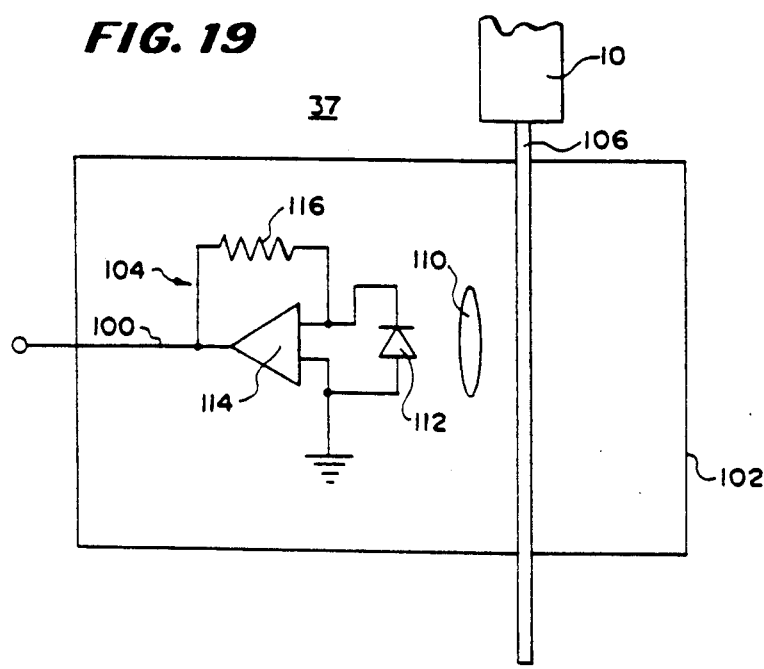
FIG. 19 is a schematic view of another portion of the embodiment of FIG. 8.

In FIG. 19, there is shown a schematic circuit diagram of a light feedback unit 37 (FIG. 8) having an electrical conductor 100, a transmitting fiber optic light conductor 106 of the bundle 40 (FIG. 8), an opaque housing 102 and an optical sensor 104. The light feedback unit 37 develops a signal on conductor 100 for application to the monitor system 22 (FIG. 8) related to light transmitted through the fiber optic conductor 106 through the opaque housing 102 which is an opaque interface between the laser system 10 and the casing 74 for the light interface system 20 (FIG. 8).

To develop a feedback signal for application to the monitor system 22 (FIG. 8) the feedback unit 37 includes an optical sensor 104 having a lens 110, a light sensing diode 112, an amplifier 114 and a resistor 116. The lens 110 receives light from the leakage spot through the fiber optic conductor 106 and transmits it to the light sensing diode 112, which has its cathode electrically connected to one input of the amplifer 114 and its anode electrically connected to ground and to the other input of the amplifier 114. The resistor 116 is a feedback resistor between the cathode of the light sensing diode 112 and the output of the amplifier 114.

The conductor 100 is electrically connected to the output of the amplifier 114 to provide a signal related to the light intensity impinging upon the sensing diode 112. This signal may be used for control and monitoring purposes.

Figure 20:
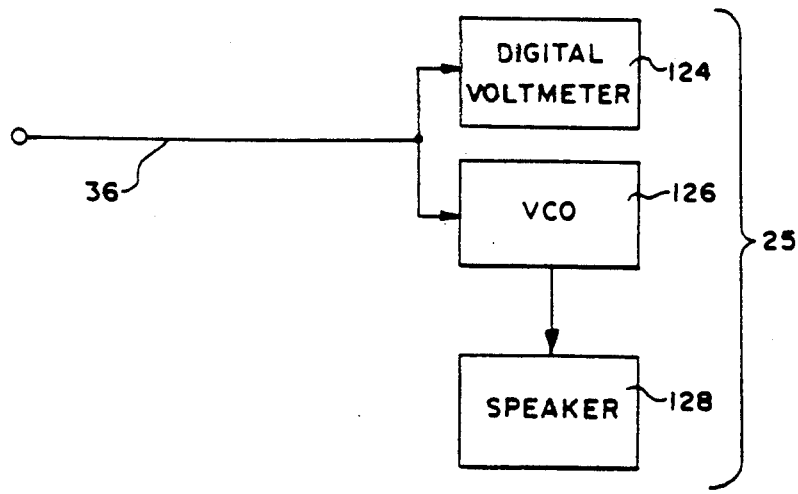
FIG. 20 is a block diagram of still another portion of the embodiment of FIG. 9.

In FIG. 20 there is shown a block diagram of the monitor system 22A having the readout 25 (FIG. 8) which includes in the preferred embodiment a digital volt meter 124, a voltage control oscillator 126 and a speaker 128. The photodiode 28 (FIG. 8) is electrically connected to readout 25 through conductor 36 and converts the current signal from the sensor to a voltage output, which voltage output represents the amount of illumination from the treatment area. This may be further processed for use in the power control 23 if desired.

To provide a read-out of the amount of fluorescence resulting from a known intensity of light on a treated area, the conductor 36 is electrically connected to the digital volt meter 124 and to the voltage control oscillator 126. The digital volt meter 124 is read directly and the voltage control oscillator 126 generates an alternating current voltage which is applied to the speaker 128 to provide an audible signal, the pitch of which indicates the amount of fluorescence.

Although a digital volt meter and a speaker are used for visual and audible indications to the user, other read-out techniques may be used and a signal, although not used in the preferred embodiment, may be applied to the lasers to alter intensity or frequency or both in a feedback system. The signal may also be utilized to generate a signal for visual interpretation on an oscilloscope or to be applied to data processing equipment for conversion to digital form and for further calculations. Moreover, it may be recorded on a chart or graph for analysis later.

TESTS

While tests using the new drug have been performed principally on animals, it is believed that equivalent results will be obtained on humans, utilizing the same or less relative amount of drug to body

TABLE II

| PATIENT IDENTIFICATION | DOSE $\frac{mg}{kg}$ OF DRUG | % OBSTRUCTION | LIGHT DOSE | RESPONSE |
| --- | --- | --- | --- | --- |
| AP 164766 | 2.0<br>2.0<br>2.0<br>2.0 | Right Upper Lobar Bronchus = very small nodule<br>Left Main Bronchus Stem = 5 × 3 mm | 400 mw/cm-1.5 cm cyl.- for delivery 720 J/cm<br>(1) 500 mw/cm - 3 cm cylinder<br>(2) 400 mw/cm - 3 cm cyl. - 200 J/cm<br>(3) Same as #2<br>(4) Same as #2 | Complete Response both tumors |
| HW 167259 | 2.0<br>3.0 (Hpd) | (L.) Bronchial Stump Recurrence - s/p left pneumonectomy | 540 J-1 cm cylinder - implant<br>400 mw/cm-3 cm cylinder - implant | #1 Partial Response 25%<br>#2 Progession -<br>Started on Chem |
| FW 167165 | 2.0 | Left mam Bronchus Stem = 100% | 1 om cylinder - 200 J/cm implant<br>Repeated × 1 | No Response at 48 hrs. post Rx<br>Expired at home 5 wks after Rx |
| PS 168674 | 2.0 | Right Main Bronchus Stem = 70%, also partial occlusion of Left Main Bronchus Branch and trachea Surgery | 500 mw/cm - 3.3 cm. cylinder - (750 J) | Partial Response - however disease progressed - expired |

TABLE III

| PATIENT IDENTIFICATION | DOSE | % OBSTRUCTION | LIGHT DOSE | RESPONSE |
| --- | --- | --- | --- | --- |
| MQ 1686 | 2.0 | Right Main Bronchus Stem = 100%<br>Trachea = >50% | 480 mw/cm - 2.5 cm. cylinder - 250 J/cm - implant<br>Surface: 2.5 cylinder 125 J/cm | No response - expired; Respiratory failure 2 months - post Rx |
| HN 167419 | 2.0 | Right Main Bronchus Stem = >90% | 600 mw/cm - 1 cm cylinder 540 J/cm - implant × 3 | Partial response at 4 days - post Rx<br>Expired 5 wks after Rx - hemmorhage |
| MM 167389 | 2.0 | Left Main Bronchus Stem >90% | 600 mw/cm × 15 mins. - 1 cm cylinder - 540 J/cm - implanted × 3 | No change at 72 hrs. - expired from pneumonia 3 wks post PDT - massive involvement |
| DL 167080 | 2.0 | Left Main Bronchus Stem >50% | 500 mw/cm - 1.2 cm cylinder 450 J/cm × 2 - Implanted | Partial response expired from respiratory arrest (brain and bone mets.) |
| WH 168271 | 2.0 | Left Main Bronchus Stem ~90% | 400 mw/cm - 3 cm cylinder 200 J/cm - treated S + interstitial simultaneously - apparently 2 separate tumors | No response - expired 5 weeks post Rx - massive disease |

TABLE IV

| PATIENT IDENTIFICATION | DOSE | % OBSTRUCTION | LIGHT DOSE | RESPONSE |
| --- | --- | --- | --- | --- |
| JJ 167585 | 1.5 | Right Main Bronchus Stem ~75%<br>Left Main Bronchus ~75% | Day 3 = 400 mw/cm cylinder 200 J/cm (8.5 min)<br>Day 7 = 400 mw/cm - 3 min cyl 312 J/cm (13 min) | ~25% response - expired 1 month post PDT - pulmonary hemorrhage |

TABLE IV-continued

| PATIENT IDENTIFICATION | DOSE | % OBSTRUCTION | LIGHT DOSE | RESPONSE |
| --- | --- | --- | --- | --- |
| MG 167240 | 2.0 | Right Main Bronchus Stem = 100% | 350 mw/15 mins - straight fiber implanted × 2 times - 315 J/cm and surface PDT - 400 mw total × 5 mins 1200 J/cm | No Response |
| | 2.4 - | | 400 mw × 8.5 mins on 1 cm cylinder 200 J/cm - implanted × 3 | Some Response - 20%-30% Expired - pneumonia |
| RF 166144 | 2.0 | Right Main Bronchus Stem - 100% with extension to Left Main Bronchus Stem | 500 mw/cm × 20 mins - 3.2 cylinder Implanted - 600 J/cm | No Response |
| | 3.0 | | 300 mw/cm × 30 mins - 3 cm cylinder Implanted - 540 J | No Response - expired - hemorrhage |
| LR 169121 | 2.0 | Trachea | 400 mw/cm - 3 cm cylinder 200 J/cm (8.5 mins) × 2 | Some Response - started chemo |

TABLE V

| PATIENT IDENTIFICATION | DOSE | % OBSTRUCTION | LIGHT DOSE | RESPONSE |
| --- | --- | --- | --- | --- |
| SM 166462 | 2.0 | Right Main Bronchus Stem ~50% S/P - Right Upper Lobectomy | 500 mw/cm × 20 mins - 3 cm cylinder - 600 J/cm | Marked decrease of tumor protrusion into lumen at 6 days PDT - did not return |
| DS 161223 | 2.0 | Left Main Bronchus Stem = 70% | 400 mw/cm × 8 mins and 500 mw/cm × 13 mins - both 3 cm cylinders - 200 J/cm and 400 J/cm | Partial response receiving chemo |
| EB 169173 | 2.0 | L.L.L. = >90% | 400 mw/cm × 8.5 mins - 3 cm cylinder - 200 J/cm | Partial response 4 days post PDT |
| WE 167155 | 2.0 | Right Main Bronchus Stem = +50% | 500 mw/cm × 20 - 3 cm cylinder - 600 J/cm | Partial response 6 months post PDT - hemorrhage |
| RF 165513 | 2.0 | Right Bronchus Intermedius = 80% | 400 mw/lin cm × 8 mins = 3 cm cylinder - 192 J/cm | No response - expired 5 days post PDT - handle secretions extensive involvement - expired - pneumonia cause of death: pneumonia | weight. Tests have been, to a limited extent, performed on humans with endobronchial tumors to support this opinion as shown in tables II, III, IV and V. It is believed that the aforedescribed treatment utilizing the drug of the invention, can be used repeatedly without cumulative damage to normal tissues, providing that treatment is not overly aggressive. This is supported by the data of tables II, III, IV and V as well. Furthermore, recent tests of patients utilizing the drug DHE at doses to produce equal or better results compared to the prior art drug have resulted in markedly lower toxicity of healthy tissue in lung cancer patients.

While the aforementioned animal tests utilized a dosage of the new drug of approximately 4 mg/kg of body weight, in the treatment of the tumors in humans, dosages as low as 1 mg/kg of body weight are believed effective in utilizing the new drug. In any event dosages of the new drug of only approximately one-half of the prior art dosages are equivalently effective in accomplishing necrosis of tumors.

Also, while the aforementioned animal tests utilized illumination one day following injection of the new drug and the human tests 2 to 3 days, it is believed that a delay of up to seven days prior to illumination still will accomplish necrosis, and a time delay of three hours to three days between injection and illumination is generally believed at this time preferable in humans in order to achieve the best therapeutic ratio of drug in undesirable tissue to drug in normal tissue. However, it is believed that these differ in various types of tissues. The optimum therapeutic ratio can be determined by experience and measurement of fluorescence and the ratio which provides destruction of the undesirable tissue with minimum change to the normal tissue is selected based on the drug level in both the undesirable and normal tissue.

Furthermore, while an intensity of 160 mw/cm$^2$ for 30 minutes was utilized to activate the drug, it is believed that an intensity as high as 1 watt/cm$^2$ for 20 minutes or as low as 5 mw/cm$^2$ for an extended period of time may be utilized to accomplish necrosis. Less than 5 mw/cm$^2$ of illumination intensity will probably have no therapeutic effect, irrespective of time of application. More than 400 mw/cm$^2$ may cause undesirable thermal effects in some cases. For inserted cylindrical fibers, powers in the range of 50 to 500 mw/cm of emitting length are used without thermal effects or above 500 mw/cm if thermal effects are desired.

DBA2 Ha/D mice were transplanted with SMT-F tumors. When the transplanted tumors reached 5-6 mm (millimeters) in diameter, the mice were injected with a dose of 7.5 milligrams of the crude prior art Lipson derivative per kilogram of body weight for comparison purposes.

Approximately 24 hours following the injection, the tumor areas of the mice were shaved to remove the fur. The mice were exposed to red light (600-700 mw) from an arc lamp at an intensity of 160 mw (milliwatts) per square centimeter for 30 minutes. Ten of twenty mice showed no apparent tumors seven days after treatment.

The injected drug is retained in the tumor cells longer as compared to normal tissue.

This protocol was repeated using the new drug disclosed in this invention and equivalent results were obtained but using a drug dose of approximately one-half (4 mg/kg of body weight), as compared to the prior art Lipson drug.

In further tests ICR Swiss (Albino) mice were injected with a therapeutic dose of the crude Lipson derivative (7.5 mg/kg of body weight). Approximately 24 hours following such injection, the hind feet of the mice were exposed to the same light conditions used in the aforesaid tumor response study. The damage to the hind feet was assessed as 2.0 on an arbitrary scale where 0.0 is no damage and 5.0 is complete necrosis.

| Injected Dose (mg/kg) | TISSUE LEVELS OF $^3$H-HPD AND $^3$H-DHE ($\mu$g/g wet tissue) DBA/2 Ha MICE, SMT-F TUMOR | | | | | | | |
|---|---|---|---|---|---|---|---|---|
| | Liver | Kidney | Spleen | Lung | Muscle | Brain | Skin | Tumor |
| 10 - Hpd 24 h | 14.2 ± 2 | 9.7 ± 2.1 | 7.1 ± 1.2 | 1.9 ± 0.4 | 0.76 ± 0.25 | 0.33 ± 0.15 | 3.5 ± 1.2 | 3.6 ± 1.1 |
| 5 - DHE 24 h | 19.1 ± 3.3 | 8.3 ± 2.3 | 8.1 ± 2.9 | 2.7 ± 1.4 | 0.68 ± 0.26 | 0.19 ± 0.1 | 3.4 ± 1.3 | 3.5 ± 1.2 |
| 10 - Hpd 72 h | 13.8 ± 6 | 7.3 ± 3 | 6.1 ± 1.1 | 2.3 ± 0.9 | 1.2 ± 0.7 | 0.7 ± 0.4 | 2.8 ± 1.9 | 2.3 ± 1.08 |
| 5 - DHE 72 h | 15 ± 4 | 7.6 ± 2.5 | 6.6 ± 1.4 | 2.3 ± 0.8 | 1.9 ± 0.6 | 0.9 ± 0.6 | 1.9 ± 0.6 | 1.6 ± 0.5 |

Minimum number of animals per tissue was 10. maximum 17. Tumor volume double is approximate 3 days.

Moist desquamation was evident and the foot area slowly returned to normal after about 40 days. This protocol was repeated using the new drug disclosed in this application in doses of 4 mg/kg of body weight. Only slight erythema and/or edema was noticed following treatment for a score of less than one on the aforementioned scale of damage. This condition disappeared after 48-72 h (hours) with no residual effects. This leads us to believe that skin photosensitivity may no longer be a significant problem when using this new drug.

A summary of further tests on animals is shown in table one for mice comparing unpurified HPD and the purified DHE new drug indicating drug levels in mice.

From the foregoing description and accompanying drawings, it will be seen that the invention provides a new and novel drug, useful in the diagnosis and treatment of tumors, permitting utilization of reduced amounts of the drug as compared to related prior art drugs and which results in less severe side effects. The invention also provides a novel method of producing the new drug, together with a novel method of utilizing the drug in the treatment of tumors.

The terms and expressions which have been used are used as terms of description and not of limitation and there is no intention in the use of such terms and expressions of excluding any equivalents of any of the features shown or described, or portions thereof. Moreover, various modifications in the preferred embodiment are possible within the scope of the claimed invention.

What is claimed is:

1. A method to diagnose the presence or absence of tumor tissue at a location in a subject which method comprises administering to said subject an effective amount of a composition consisting essentially of 10 kd aggregates of porphyrins which are fluorescent, photosensitizing and capable of localizing and being retained in tumor cells for a longer time than in normal tissues, and wherein the process for preparation of said composition comprises raising the pH of a hematoporphyrin derivative preparation in aqueous medium to 6.5-12 to obtain aggregates of 10 kd or greater and separating said aggregates from the remainder of the hematoporphyrin derivative preparation in an amount effective to localize in a tumor at said suspected location;

waiting for sufficient time to permit the drug to clear normal tissue;

irradiating the suspected location with a wavelength absorbed by, and which elicits fluorescence from, said composition; and measuring the fluorescence emitted.

2. The method of claim 1 wherein said waiting time is about 3 hours-2 days.

* * * * *